United States Patent
Kilian

(10) Patent No.: US 6,713,258 B2
(45) Date of Patent: Mar. 30, 2004

(54) METHODS FOR GENOTYPING BY HYBRIDIZATION ANALYSIS

(75) Inventor: Andrzej Kilian, Kaleen (AU)

(73) Assignee: Center for the Application of Molecular Biology to International Agriculture (Cambia), Black Mountain (AU)

(*) Notice: Subject to any disclaimer, the term of this patent is extended or adjusted under 35 U.S.C. 154(b) by 0 days.

(21) Appl. No.: 09/820,328

(22) Filed: Mar. 29, 2001

(65) Prior Publication Data

US 2002/0042063 A1 Apr. 11, 2002

Related U.S. Application Data

(60) Provisional application No. 60/252,747, filed on Nov. 22, 2000, provisional application No. 60/252,551, filed on Nov. 21, 2000, and provisional application No. 60/193,042, filed on Mar. 29, 2000.

(51) Int. Cl.[7] .......................... C12Q 1/68; C12P 19/34; C12M 1/34; C07H 21/02; C07H 21/04

(52) U.S. Cl. .................... 435/6; 435/91.1; 435/91.2; 435/287.2; 536/23.1; 536/24.3; 536/24.33

(58) Field of Search .................... 435/6, 91.1, 91.2, 435/183, 287.1, 287.2; 436/94, 501; 536/23.1, 24.3, 24.33, 25.3, 25.32

(56) References Cited

U.S. PATENT DOCUMENTS

| | | | |
|---|---|---|---|
| 5,126,239 A | 6/1992 | Livak et al. .................. | 435/6 |
| 5,262,311 A | 11/1993 | Pardee et al. .............. | 435/91.2 |
| 5,320,814 A | 6/1994 | Walt et al. ............... | 422/82.07 |
| 5,413,909 A | 5/1995 | Bassam et al. ................ | 435/6 |
| 5,437,975 A | 8/1995 | McClelland et al. .......... | 435/6 |
| 5,487,985 A | 1/1996 | McClelland et al. ........ | 435/91.2 |
| 5,508,169 A | 4/1996 | Deugau et al. ................ | 435/6 |
| 5,576,180 A | 11/1996 | Melanon et al. ............... | 435/6 |
| 5,580,726 A | 12/1996 | Villeponteau et al. ......... | 435/6 |
| 5,665,572 A | 9/1997 | Ikeda et al. ................ | 435/91.2 |
| 5,667,976 A | 9/1997 | Van Ness et al. ............... | 435/6 |
| 5,710,000 A | 1/1998 | Sapolsk et al. ................ | 435/6 |
| 5,712,126 A | 1/1998 | Weissman et al. ......... | 435/91.2 |
| 5,728,524 A | 3/1998 | Sibson ......................... | 435/6 |
| 5,814,524 A | 9/1998 | Walt et al. ................. | 436/518 |
| 5,858,656 A | 1/1999 | Deugau et al. ................ | 435/6 |
| 5,861,245 A | 1/1999 | McClelland et al. .......... | 435/6 |
| 5,874,215 A | 2/1999 | Kuiper et al. .................. | 435/6 |
| 5,876,933 A | 3/1999 | Perlin | |
| 5,986,085 A | 11/1999 | Gjerde et al. ............ | 536/25.41 |
| 5,994,065 A | 11/1999 | Van Ness ..................... | 435/6 |
| 5,994,068 A | 11/1999 | Guilfole et al. ................ | 435/6 |
| 5,997,742 A | 12/1999 | Gjerde et al. ................ | 210/635 |
| 6,045,994 A | 4/2000 | Zabeau et al. .................. | 435/6 |
| 6,100,030 A | 8/2000 | McCask Feazel et al. ...... | 435/6 |
| 6,248,521 B1 * | 6/2001 | Van Ness et al. ............... | 435/6 |

FOREIGN PATENT DOCUMENTS

| | | |
|---|---|---|
| EP | 0 967 291 A1 | 12/1999 |
| EP | 0 976 836 A1 | 2/2000 |
| WO | 97/17413 | 5/1997 |
| WO | WO 97/22720 A1 | 6/1997 |
| WO | 98/00721 | 1/1998 |
| WO | WO 98/30721 | 7/1998 |
| WO | WO 98/30721 A1 | 7/1998 |
| WO | 98/50782 | 11/1998 |
| WO | 99/05319 | 2/1999 |
| WO | WO 99/05324 A1 | 2/1999 |
| WO | 99/18434 | 4/1999 |
| WO | WO 99/43855 A1 | 9/1999 |
| WO | 99/45357 | 9/1999 |
| WO | WO00/18960 | 4/2000 |
| WO | WO 00/34518 * | 6/2000 |
| WO | WO 00/77260 A1 | 12/2000 |

OTHER PUBLICATIONS

Schena et al., Parallel human genome analysis: Mircoarray-based expression monitoring of 1000 genes. Proc. Natl. Acad. Sci. USA, 93, 10614–10619, 1996.*

Behr et al., "Comparative Genomics of BCG Vaccines by Whole–Genome DNA Microarray", *Science*, May 28, 1999, vol. 284, pp. 1520–1523.

Gingeras et al., "Simultaneous Genotyping and Species Identification Using Hybridization Pattern Recognition Analysis of Generic Mycobacterium DNA Arrays", *Genome Research*, 1998, pp. 435–448, Cold Spring Harbor Laboratory Press.

Botstein et al, "Construction of a genetic linkage map in man using restriction fragment length polymorphisms", Am. J. Hum. Genet, 32:314–331, 1980, American Society of Human Genetics.

Bureau et al, "A computer–based systematic survey reveals the predominance of small inverted–repeat elements in wild–type rice genes", Proc. Natl. Acad. Sci. 93:8524–8529, 1996, Natl. Academy of Sciences.

(List continued on next page.)

Primary Examiner—Ethan Whisenant
Assistant Examiner—Frank W Lu
(74) Attorney, Agent, or Firm—Foley and Lardner

(57) ABSTRACT

This invention provides methods for determining the genotype of organisms by hybridization analysis and, more specifically, to establishing the relatedness of individual organisms within a species. The present invention provides addressable arrays, comprising diversity panels of nucleic acid molecules, in which the molecules on the array are addressable or uniquely identifiable in some fashion. A diversity panel is the result of a method that can distinguish sequence differences between nucleic acid samples. As taught herein, a variety of methods may be used to generate diversity panels. Subsequent to the generation of the diversity panel, the nucleic acid products of the diversity panel are separated for application onto an array. The separated diversity panel is then delivered onto a substrate to create an addressable array and hybridized with labeled nucleic acids. The genotype of an organism is determined by the pattern of hybridization.

22 Claims, 14 Drawing Sheets

OTHER PUBLICATIONS

Chun et al, "Rapid amplification of uncharacterized transposon–tagged DNA sequences from genomic DNA" Yeast, 13:233–240, 1997, John Wile & Sons. Ltd.

Guilfoyle et al, "Ligation–mediated PCR amplification of specific fragments from a Class–II restriction Endonuclease total digest", Nucleic Acids Research, 25(9):1854–1858, 1997, Oxford University Press.

Murra et al, "Rapid isolation of high molecular weight plant DNA", Nucleic Acids Research, 8(19):4321–4325, 1980, IRL Press Limited.

Sproer et al, "The phylogenetic position of Serratia, Buttiauxella and some other genera of the family Enterobacteriaceae", International Journal of Systematic, Bacteriolog, 49:1433–1438, 1999, IUMS.

Vos et al, "AFLP: a new technique for DNA fingerprinting", Nucleic Acids Research, 23:4407–4414, 1995 Oxford University Press.

Williams et al, "DNA polymorphisms amplified b arbitrary primers are useful as genetic markers", Nucleic Acids Research, 18(22):6531–6535, 1990.

Sproer et al, "The correlation between morphological and phylogenetic classification of myxobacteria", International Journal of Systematic Bacteriology, 49:1255–1262, 1999, IUMS.

Himmelbauer H, et al., Complex probes for high–throughput parallel genetic mapping of genomic mouse BAC clones, Mamalian Genome 9: 611–616, 1998.

Huang TH, Perry MR, Laux DE, Methylation profiling of CpG islands in human breast cancer cells, *Human Molecular Genetics* 8 (3): 459–470, 1999.

Penner GA, et al., Rapid RAPD screening of plant DNA using dot blot hybridization, *Molecular Breeding* 2: 7–10, 1996.

Yoshida Y, et al., Development of the arbitrarly primed–representational difference analysis method and chromosomal mapping of isolated high throughput rat genetic markers, *Proc. Natl. Acad. Sci.* vol. 96: pp. 610–615, Jan. 1999.

Jaccoud et al., "Diversity Arrays: a solid state technology for sequence information independent genotyping," *Nucleic Acids Research* (2001), vol. 29, No. 4 e26, pp. 1–7, Oxford University Press.

Ushijima et al., "Isolation of 48 genetic markers appropriate for high throughput genotyping of inbred rat strains by B1 repetitive sequence–representational difference analysis," *Mammalian Genome* (1998), vol. 9, pp. 1008–1012, Springer–Verlag New York Inc.

Jordan et al., "Genome complexity reduction of SNP genotyping analysis," *PNAS* (Mar. 5, 2002), vol. 99, No. 5, pp. 2942–2947, www.pnas.org/cgi/doi/10.1073/pnas.261710699.

* cited by examiner

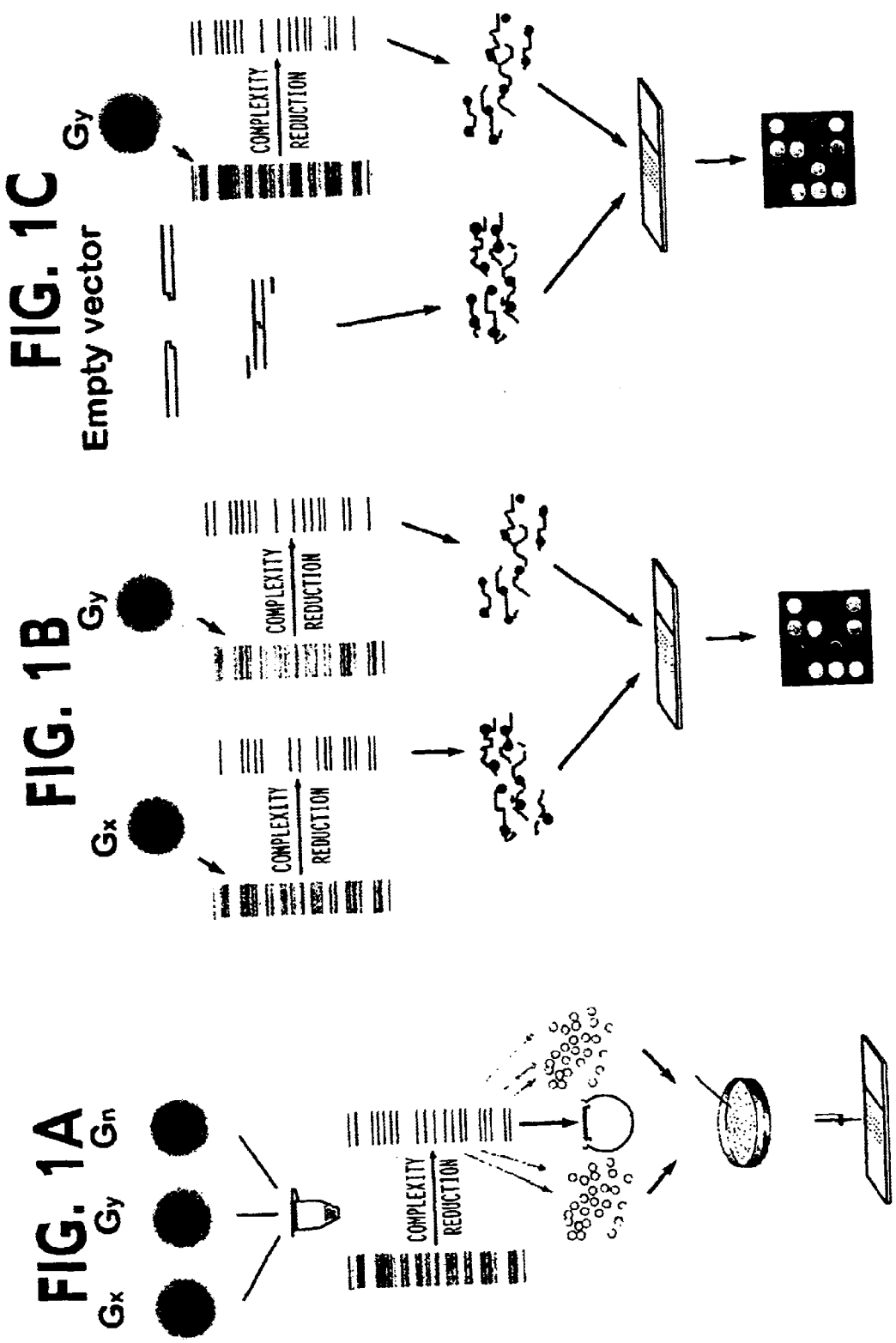

IR20 Green Cy3
Millin Red Cy5

IR64 Green Cy3
Millin Red Cy5

IR20 Green Cy3
Millin Red Cy5

FIG.6B 1 mm
IR20 Green CY3
Vector Red Cy5

Barley DArT polymorphism analysis between Steptoe and Morex cultivars

Morex Diversity Panel was labelled with Cy3 and Steptoe Diversity Panel with Cy5 dyes Mouse DArTs using cDNA-based Diversity Array Methylation pattern differences among rice tissues typed using DArTs Red: callus
Green: seedling root
Yellow: callus + root Red: callus
Green: immature embryo
Yellow: callus + embryo Amplicon Southern analysis

SEQUENCE LISTING

```
<160> NUMBER OF SEQ ID NOS: 21

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 1
ctcgtagact gcgtacc                                                    17

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Adapter
```

```
                           sequence

<400> SEQUENCE: 2
aattggtacg catgctac                                                      18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (18)
<223> OTHER INFORMATION: a, g, c or t

<400> SEQUENCE: 3
gactgcgtac caattcanr                                                     19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Adapter
       sequence

<400> SEQUENCE: 4
cacgatggat ccagtgca                                                      18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Adapter
       sequence

<400> SEQUENCE: 5
ctggatccat cgtgcag                                                       17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6
gatggatcca gtgcagt                                                       17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Adapter
       sequence

<400> SEQUENCE: 7
gactgtagac tgcgatg                                                       17

<210> SEQ ID NO 8
<211> LENGTH: 16
<212> TYPE: DNA
<213> ORGANISM: Artificial Sequence
<220> FEATURE:
```

<223> OTHER INFORMATION: Description of Artificial Sequence: Adapter
      sequence

<400> SEQUENCE: 8
cgcatcgcag tctaca                                                    16

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
gtagactgcg atgcggtg                                                  18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 10
cacgatggat ccagtgca                                                  18

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 11
ctggatccat cgtgcag                                                   17

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 12
gatggatcca gtgcag                                                    16

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (17)
<223> OTHER INFORMATION: a, c, g or t

<400> SEQUENCE: 13
gatggatcca gtgcagn                                                   17

<210> SEQ ID NO 14
<211> LENGTH: 16
<212> TYPE: DNA
<213> ORGANISM: Artificial Sequence
<220> FEATURE:

<223> OTHER INFORMATION: Description of Artificial Sequence: Primer

<400> SEQUENCE: 14
gatggatcca gtgcag                                                          16

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
accgtgtcgc tgtcctaaac                                                      20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
atattcccaa ggtttgactt                                                      20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
ctttacgagt atggagggag                                                      20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 18
ctcgtagact gcgtacc                                                         17

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 19
tactcaggac tcat                                                            14

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)..(30)
<223> OTHER INFORMATION: a, c, g or t

<400> SEQUENCE: 20

```
ggccacgcgt cgactagtac nnnnnnnnnn tcgag                         35
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21

```
ggccacgcgt cgactagtac                                          20
```

METHODS FOR GENOTYPING BY HYBRIDIZATION ANALYSIS

Applicant claims priority to the corresponding foreign application 60/193,042 filed Mar. 29, 2000 60,252,551 filed Nov. 21, 2000 and 60/252,747 filed Nov. 22, 2000.

FIELD OF THE INVENTION

This invention relates generally to determining the genotype of organisms by hybridization analysis and, more specifically, to establishing the relatedness of individual organisms within a species.

BACKGROUND OF THE INVENTION

A genotype is the genetic constitution of an individual or group. Variations in genotype are essential for commercial breeding programs, diagnostics, monitoring genetic-based diseases, following spread of pathogens, determining parentage, and the like. While determining the nucleic acid sequence of genomic DNA is one way to unambiguously establish a genotype of an individual, it is not currently practicable to accomplish, especially in organisms with complex genomes.

Genotypes can be more readily described in terms of genetic markers. A genetic marker identifies a specific region or locus in the genome. Thus, the more genetic markers, the finer defined is the genotype. A genetic marker becomes particularly useful when it is allelic between organisms because it then may serve to unambiguously identify an individual.

Many different flavors of genetic markers have been described and exploited, but all are based upon genomic sequence. Examples of methods to define genetic markers include restriction fragment length polymorphism (RFLP) analysis (Botstein et al., *Am J Hum Genet* 32: 314, 1980); single-sequence repeats (SSR) analysis (Weber and May,*Am J Hum Genet* 44: 388, 1989; U.S. Pat. No. 5,874,215); rapid-amplified polymorphic DNA (RAPD); amplified fragment length polymorphism (AFLP) (Vos et al., *Nucleic Acids Res* 23: 4407, 1995); 5' nuclease amplifications (U.S. Pat. No. 5,962,233); nucleic acid indexing (U.S. Pat. No. 5,994,068; Guilfoyle, et al., *Nucl Acids Res,* 25; 1854, 1997; Unrau and Degau., *Gene* 145: 163, 1994; U.S. Pat. No. 5,508,169) arbitrarily-primed nucleic acid amplification (U.S. Pat. No. 5,413,909; U.S. Pat. No 5,861,245); restriction enzyme amplification display system (READS) (U.S. Pat. No. 5,712,126; Prashar and Weissman, *Proc Natl Acad Sci USA* 93: 659, 1996); consensus sequence primed polymerase chain reaction (CP-PCR) (U.S. Pat. No. 5,437,975); hybridization-based genetic amplification (WO 98/0721); and the like.

All of these genotyping methods suffer from the laborious requirement to analyze only a single organism at a time. A further burden in some of these methods is the need for pre-identification of a polymorphism before analysis of other individuals (U.S. Pat. No. 6,100,030). Still others of these methods depend upon expensive materials and time-intensive gel electrophoresis, resulting in a low-throughput. Furthermore, these methods that base identity on size suffer from additional difficulties in precisely correlating bands on gels with alleles. One method has attempted to overcome many of these restrictions by performing analysis by hybridization to nucleic acids immobilized on solid-state surfaces (U.S. Pat. No. 6,100,030). In this technique however, a genotype of an organism is not established. Rather, the analysis yields information regarding a pre-determined polymorphism.

The ability to assign a comprehensive genotype for an individual without requiring sequence information, existing knowledge of polymorphisms, or having to compare lengths is paramount to the mass of genetic information necessary for breeding, disease analysis, and so forth. Such systems and analyses also demands a high-throughput for optimal and maximal benefit.

The present invention discloses methods and compositions for performing high throughput genotype determinations by basing analyses on hybridization of unselected nucleic acids to genomic nucleic acids immobilized to solid state materials, and further provides other related advantages.

SUMMARY OF THE INVENTION

The present invention relates to methods and compositions for determining and relating genotypes of organisms. Within one aspect of the present invention, a nucleic acid molecule that contains a polymorphism is identified. Two organisms are selected, one may be referred to as a reference organism and the other may be referred to as the tester organism. Nucleic acids from each of these organisms are separately amplified. Amplified material from the tester organism is cloned or otherwise separated (by e.g., gel electrophoresis, HPLC), and individual clones or separated amplified material is placed into an addressable array. The amplified material from the reference organism, which contains a detectable label is hybridized to the array. Clones on the array that do not evidence detectable hybridization are thus identified as containing a polymorphism.

In a second aspect, the genotype of an organism is determined. In this method, nucleic acids from two or more organisms are pooled and used to generate a first diversity panel. In one embodiment, the diversity panel is generated by amplification. In other embodiments, the diversity panel is generated by restriction enzyme digestion, a combination of amplification and restriction digestion, or other means that creates a reproducible pattern. The first diversity panel is then separated on the basis of sequence or molecular weight, e.g., by cloning, gel electrophoresis, HPLC, or the like, and individual elements of the diversity panel, e.g., clones, are placed into an addressable array. Nucleic acids from another organism, which may be one of the organisms in the initial pool, the selected organism, is used to generate a second diversity panel.

In one aspect, the polymorphisms detected are caused by insertion elements, such as transposons. The diversity panels are generated by amplification, and in some embodiments amplification in conjunction with restriction enzyme digestion and ligation of adapters. Amplification is performed with a primer pair in which one of the primers anneals to a sequence found in a family of insertion elements.

In certain embodiments, the first and second diversity panels are generated by the same technique and using the same primers, enzymes, or methods. In other embodiments, the techniques differ, and in yet other embodiments, the techniques are the same but the primers or enzymes used to generate the two diversity panels are different.

In a preferred embodiment, the second diversity panel contains a detectable label, such as a fluorochrome, chemiluminescent molecule, radiolabel, enzyme, ligand, and the like.

The array is then hybridized with the second diversity panel. A pattern of hybridization to the array is established. The genotype of the selected organism is thus determined. Briefly, the more elements of the array that hybridize with the diversity panel of the selected organism, the more related the selected organism is to the organisms constituting the array. By generating a diversity panel from each of the organisms in the pool and hybridizing them individually to the array, the genotypes and the relatedness of all the organisms can be determined.

In a third aspect of this invention, a first diversity panel is generated and placed onto an array as described for the second aspect. The array will thus comprise the genomes of two or more organisms. A second diversity panel is generated from a selected organism, that may or may not be represented in the first diversity panel. The second diversity panel is hybridized to the array, and a pattern of hybridization is detected. The genotype of the selected organism is established.

In one embodiment, a third, fourth, and so on diversity panels are generated from individual organisms and mixed with the second diversity panel. In this embodiment, the second, third, and so on diversity panels contain a detectable label, and each diversity panel contains a label distinguishable from the others. The more labels that can be distinguished, the more diversity panels that can be mixed together. In certain embodiments, the labels are fluorochromes or mass-spectometry tags. The mixture of diversity panels is hybridized to the array, and a pattern of hybridization with each diversity panel is detected. The genotypes of the selected organisms are thus determined from the patterns of hybridization.

In a preferred embodiment, genomic nucleic acids from two or more organisms are digested with a restriction enzyme. The restriction enzyme may be an enzyme sensitive to methylation. In such a case, the polymorphisms detected are modifications (methylation) of bases. In one embodiment, fragments are selected on the basis of size to comprise a pool of fragments in a desired size range. The digested fragments are cloned into a vector and placed into an addressable array on a solid surface, such as a glass slide. Another organism whose genotype is to be determined (called here organism X), and which may or may not be the same organism as one in the first group, is digested with the same restriction enzyme. These restriction fragments are amplified. Typically, adapter sequences are ligated to the fragments and also used as primers for amplification. The amplified fragments are also labeled with one of the labels described below. Labeled fragments are hybridized to the addressable array, nonhybridized fragments are washed off, and the array is then analyzed for the label. In this way a pattern of hybridization is obtained. That pattern is the genotype of the organism X. In this example, when an element in the array hybridizes, it indicates that the organisms share sequence similarity for that fragment. When an element in the array does not hybridize, it indicates a polymorphism. In this particular example, the polymorphism is analogous to a restriction fragment length polymorphism and arises because the restriction fragment in organism X is too long to be amplified or too short to hybridize.

In still other aspects, kits and arrays are provided that comprise diversity panels for genotyping.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIGS. 1A, 1B, and 1C present a schematic representation of various embodiments of the present invention. (A) Generation of a diversity panel. Genomic DNAs of various organisms to be studied are pooled together. The DNA is cut with a chosen restriction enzyme and ligated to adapters. The complexity of the sub-genomic profile is reduced in this case by amplification using primers with selective overhangs. The amplified sub-genomic fragments are cloned. Clones are selected and inserts are amplified, purified and arrayed onto the solid support. (B) Contrasting two samples using diversity array technology. Two genomic samples are converted to diversity panels comprising sub-genomic samples. Each sub-genomic sample is labeled with a green or red fluorescent dye, mixed and hybridized to the diversity array. The ratio of green/red signal intensity is measured at each array element. Significant differences in the signal ratio indicate array elements (and the relevant fragment of the genome) for which the two samples differ. (C) Genetic fingerprinting. The DNA sample for analysis is converted to a sub-genomic sample and labeled with green fluorescent dye. Fragments of the cloning vector common to all elements of the array are labeled with red fluorescence and hybridized to the diversity panels together with the sub-genomic sample. The ratio of signal intensity is measured at each array feature. The ratios across the diversity array provide genetic fingerprint information for the sample analyzed.

FIGS. 3A and 3B. Two clones (F4 and F8), representing two polymorphic features on the EcoRI diversity panel are used as molecular probes. Four varieties of rice are analyzed simultaneously, lane 1, Bala; lane 2, Millin; lane 3, IR64, lane 4, IR20. (A) Hybridization of labeled F4 and F8 probes to Southern blots of EcoRI-digested genomic DNA. (B) Hybridization of labeled F4 and F8 probes to Southern blots of diversity panels of sub-genomic samples generated from genomic DNA samples.

FIGS. 6A and 6B show hybridization of Cy3-labeled IR20 diversity panel and Cy5-labeled Millin diversity panel (FIG. 6A) and Cy3-labeled IR20 diversity panel and Cy5-labeled vector DNA (FIG. 6B) to duplicate addressable arrays of a mixture of diversity panels.

Figure 8:
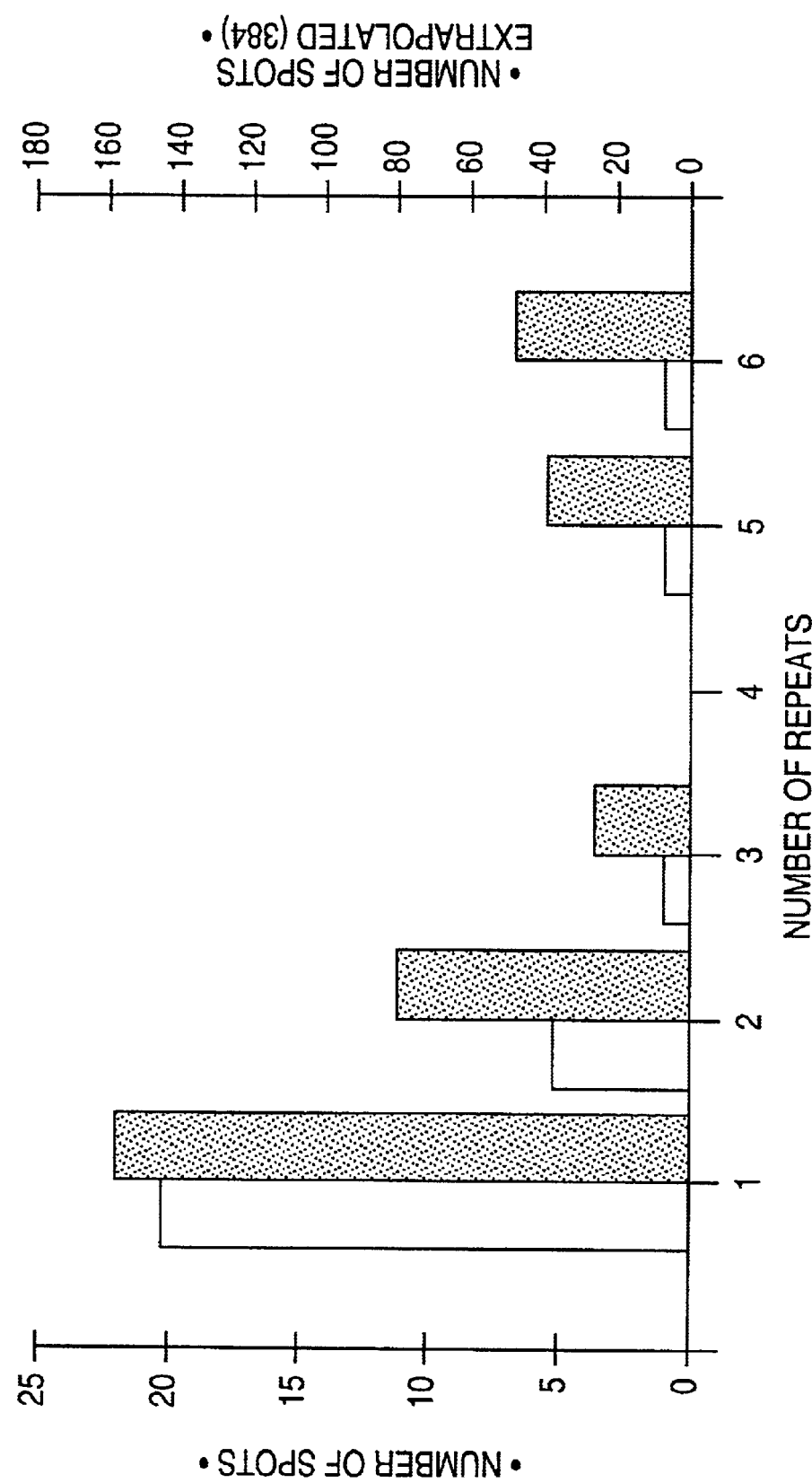

FIG. 8 presents a histogram of unique and replicate features from the MspI diversity panel. Clones are considered to be replicates if they have the same apparent gel mobility and the same polymorphism patterns among the rice cultivars analyzed. A total of 50 polymorphic spots are analyzed here. The red bars indicate the actual numbers of spots found in each category; the blue bars indicate the expected total number of spots in the diversity panel in each category by extrapolation from 50 to 384 spots in the panel.

FIG. 9 shows dendrograms generated from MspI (A) and PstI (B) diversity panels.

FIG. 10 presents the results of a reconstruction experiment using mixed (rice and several microorganisms) diversity panels. A Millin diversity panel is labeled with red fluorescent dye and an Enterobacter spiked Millin diversity panel is labeled with green fluorescent dye. The image and histogram are created using the Pathways program. (A) The left half of the array (mostly yellow features) represents rice MspI diversity array. The right half of the array contains features from MspI diversity panels from seven bacterial species and one from yeast. The green spots in the right part of the array correspond to the elements of the panel developed from the Enterobacter DNA source. (B) Histogram of the signal ratios for the array presented at (A). The Enterobacter spike is detected as the green peak seen at the left edge of the distribution.

Figure 11:
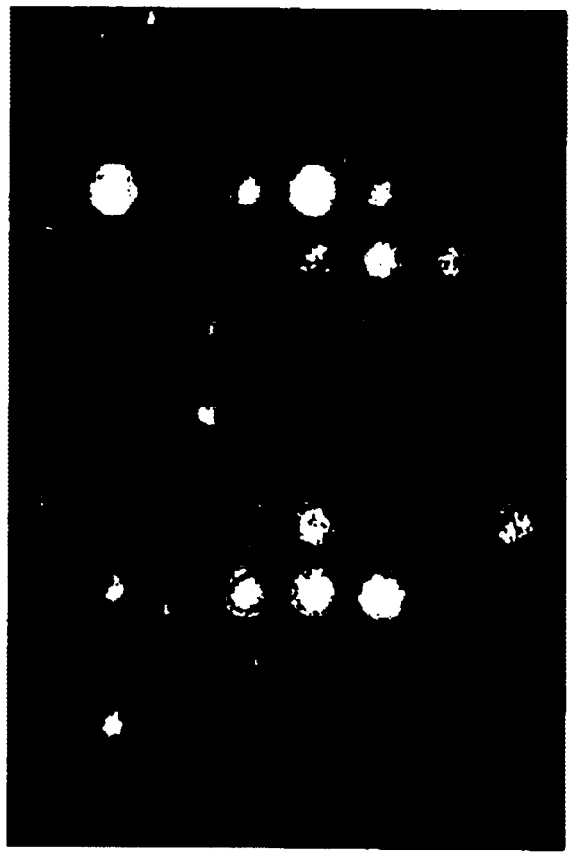

FIG. 11 presents the result of a diversity array containing DNA from 3 barley cultivars (Steptoe, Morex, Harrington) and a wild barley *Hordeum spontaneum* hybridized with Cy3-labeled Morex diversity panel and Cy5-labeled Steptoe diversity panel.

Figure 12:
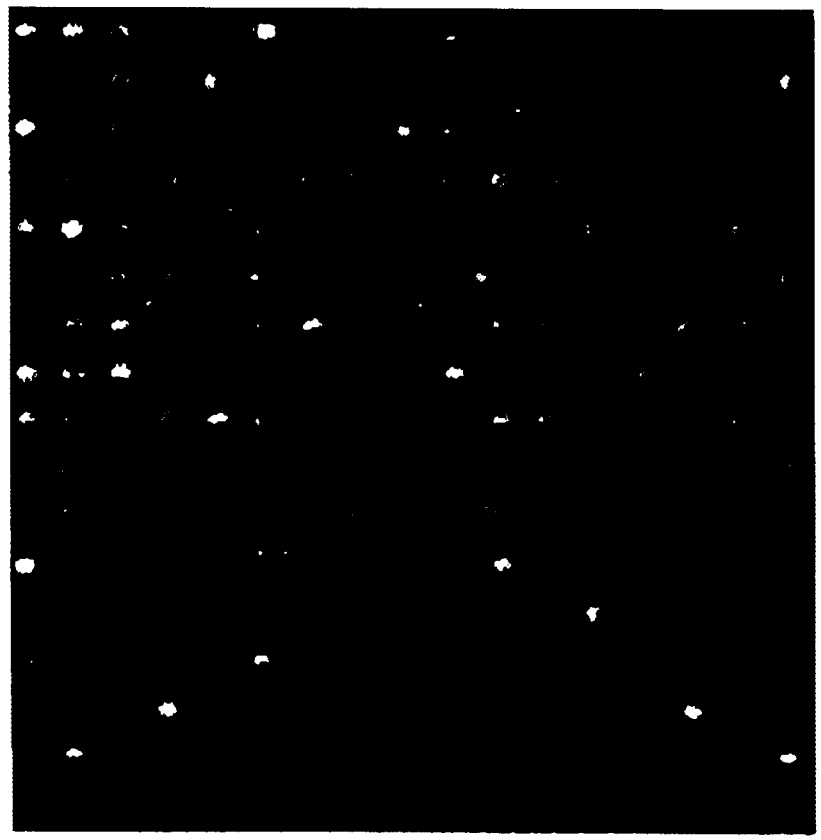

FIG. 12 presents the result of a mouse cDNA diversity array hybridized with Cy3-labeled C57BI/6 diversity panel and Cy5 labeled NOD K diversity panel.

Figure 13A:
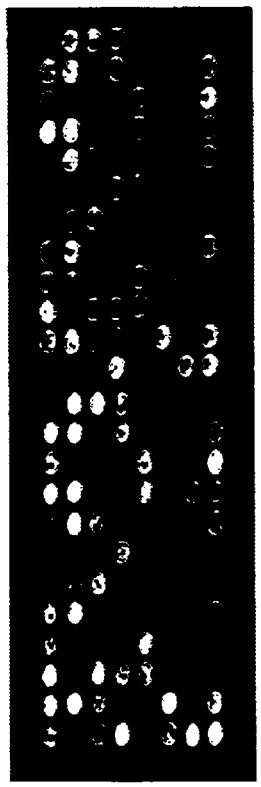
Figure 13B:
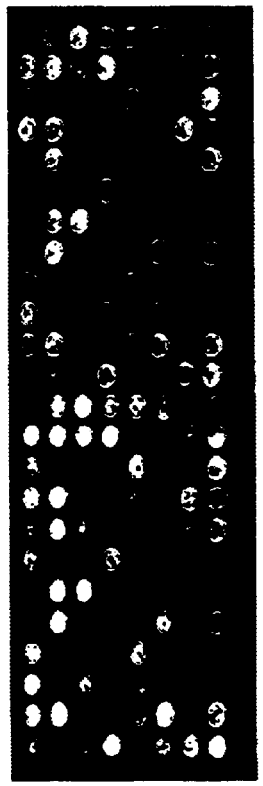

FIG. 13 presents the result of a rice diversity array hybridized with Cy5 labeled callus-diversity panel and a Cy5-labeled seedling root diversity panel (upper array) an a Cy5-labeled callus diversity panel and a Cy3-labeled immature embryo diversity panel.

Figure 14:
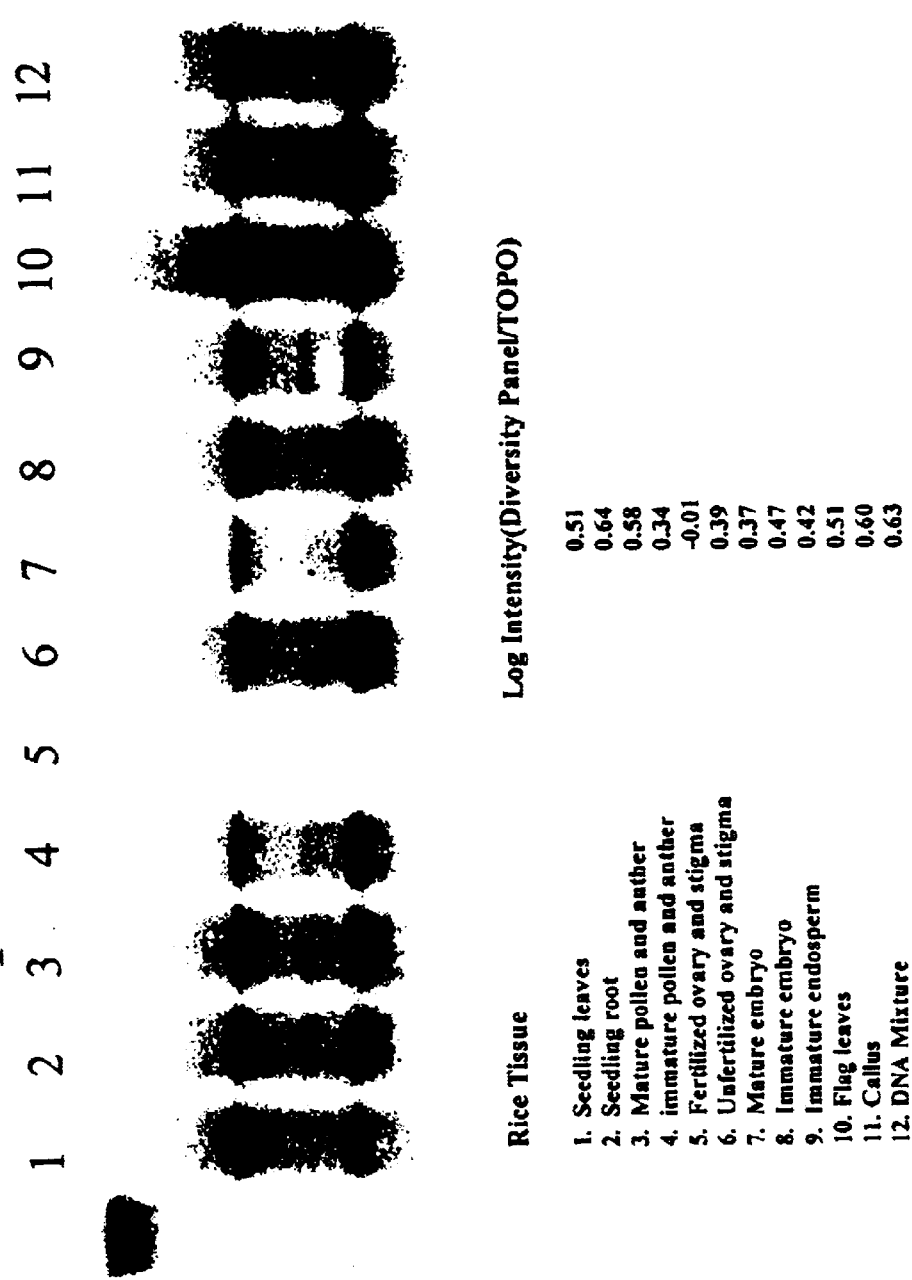

FIG. 14 presents the result of a Southern hybridization of various clones identified as differentially methylated in fertilized ovary an stigma to DNA prepared from 12 different diversity panels.

DETAILED DESCRIPTION OF THE PREFERRED EMBODIMENTS

Prior to setting forth the invention, it may be helpful to an understanding thereof to set forth definitions of certain terms that will be used hereinafter.

As used herein, an "addressable array" or an "array" means a workspace in which nucleic acid molecules are positioned in discrete locations, which can be either physically or temporally defined, such that each location is uniquely identifiable. Typically, the workspace is a solid substrate in which the locations are an identifiable pattern or at regular intervals. Examples of substrates suitable for this invention include, but are not limited to, glass slides, silicon chips, or light fiber optic tubes.

As used herein, a "fingerprint" comprises a distinct pattern of nucleic acid molecules that is a characteristic of the genotype of the organism that the nucleic acids are prepared from. The patterns can be generated by a variety of techniques, such as restriction enzyme digestion, amplification, a combination of enzyme digestion and amplification, or other method. Fingerprints can reveal sequence differences between nucleic acid samples and can be used to establish a genotype of an organism or groups of organisms. Generally, fingerprints are used to analyze and compare DNA from different species or different individuals of the same species. The differences that are detected are called polymorphisms, if pre-existing in the population, individual, or gene pool, or mutations, if exogenously or spontaneously induced or newly emergent. The precise names given to the differences, however, does not change the outcomes.

A "diversity panel" as used herein refers to nucleic acid fragments prepared from organismal nucleic acids (e.g., genomic DNA) by a method that can reveal polymorphisms or mutations (e.g., sequence differences) between samples. When a diversity panel is applied to an array, it is called herein a "diversity array."

As used herein, "organism" refers to an individual entity or a uniform set of individuals (e.g., species, strain, etc.).

As used herein, "polymorphism" and "mutation" mean a difference in DNA sequences among individuals. Differences include, without limitation, changes, modifications (e.g., methylation, bromination, amination, and the like), insertions, and deletions or combinations of these differences and may involve one or more bases.

Preparation of Arrays

The present invention provides addressable arrays, also referred to herein as arrays, comprising diversity panels of nucleic acid molecules, in which the molecules on the array are addressable or uniquely identifiable in some fashion. In the present invention, these diversity panels are generated from nucleic acid samples isolated from multiple organisms. A diversity panel refers to nucleic acid fragments prepared from organismal nucleic acids by a method that can reveal sequence differences between nucleic acid samples. As taught herein, a variety of methods may be used to generate diversity arrays.

Subsequent to the generation of the diversity panel, the nucleic acid products of the diversity panel are separated for application in a uniquely addressable format, generally onto a substrate, hereinafter called an array or an addressable array. Separation may be achieved on the basis of physical parameters, e.g., length, molecular weight, or by genetic methods, e.g., cloning.

As exemplified herein, the separated diversity panel is then delivered onto a substrate to create an addressable array. In the currently most widely used type of array, nucleic acid molecules are deposited or synthesized on a glass or silicon wafer in an ordered array. Other types of arrays can also be used, such as those that comprise nucleic acid molecules immobilized on microspheres that are uniquely encoded and randomly deposited in wells of a chemically-etched optical imaging fiber. The codes on the beads or particles permit positional registration of beads of a particular sensor type after assembly. Thus, the addressing is accomplished by the unique coding signature of each microsphere. (see, e.g., U.S. Pat. Nos. 5,814,524; 5,320,814; WO 98/50782; WO 99/18434; WO 99/45357.)

Source of Nucleic Acids

In the context of the present invention, nucleic acids for generating diversity panels are isolated from a variety of organisms. Exemplary organisms include viruses (e.g., HIV and other lentiviruses, papilloma viruses, cytomegalovirus (CMV), retroviruses, hepadnaviruses, etc.); bacteria (e.g., enterobacteria, rhizhobia, Hemophilus, etc.); plants, including commercially important crops and weedy plants; fungi, animals, including parasites (e.g., malaria, Giardia, etc.), food animals, rare or endangered species (e.g., condors, Tasmanian devils, spotted owl, etc.); and humans. Briefly, any organism for which it is desirable to assess its genotype is a suitable candidate.

The cellular source of the nucleic acids for generating diversity panels may be genomic DNA, genomic RNA, such as for retroviruses, organelle DNA, such as mitochondrial DNA, mRNA or cDNA, and the like. Methods for isolation and preparation of nucleic acid molecules are well known (see, e.g., Ausebel et al. "Current Protocols in Molecular Biology" Greene Publishing, 2000). The nucleic acid molecules used to generate diversity panels may furthermore be a mixture of two or more of these types of nucleic acids. In some embodiments, the source of the nucleic acids may be from multiple organisms or specific sub-fractions of an organism. For example, a soil sample may contain a variety of bacterial species, animals, protozoa, plant parts and the like. When using mRNA (or cDNAs) as a diversity panel, it may be desirable to choose a particular cell type or time as the source of RNA. The choice of the cellular source depends in part upon the complexity of the organism, for example a multicellular versus unicellular organism, and the intended use of the fingerprint analysis.

Methods for Generating Diversity Panels

As discussed above, generating a diversity panel entails using a method that can reveal sequence differences between nucleic acid samples. Then by determining and comparing the fingerprints of different DNA samples, the genetic relatedness of the organisms may be established.

There is a large variety of methods for generating diversity panels that are suitable within the context of this invention. Some of the more popular methods are exemplified herein. Other methods will be known to those of skill in the art. Briefly, the methods taught herein include both amplification methods and non-amplification methods. These two types of methods can also be used in combination (see Examples). As discussed above, at least two diversity panels are generated. For purposes of exemplification: one panel is arrayed onto a solid substrate and hybridized to the other panel which is in liquid phase and is the panel being fingerprinted. Either the same method or different methods may be used to generate the two or more diversity panels. While it is not necessary to reduce the complexity of the nucleic acids when generating diversity panels for this invention, at times it may be desirable to do so. Many of the methods described herein will result in a diversity panel with reduced complexity compared to the starting nucleic acids. Furthermore, the diversity panel that is being fingerprinted can be a subset or a superset of the diversity panel that is arrayed. In preferred embodiments, the probing diversity panel is a superset of the arrayed diversity panel.

Amplification Methods

A wide variety of amplification methods may be used to generate diversity panels. Such methods include adapter-mediated amplification (U.S. Pat. No. 5,710,000); U.S. Pat. No. 5,728,524, AFLP (U.S. Pat. No. 6,100,030) and other indexing methods (U.S. Pat. Nos. 5,994,068; 5,858,656; 5,508,169), arbitrarily-primed polymerase chain reaction (U.S. Pat. Nos. 5,487,985; 5,413,909; 5,126,239; 5,861,245; 5,126,239); restriction endonuclease amplification and display of cDNAs (U.S. Pat. No. 5,712,126) and other differential display methods (U.S. Pat. Nos. 5,262,311; 5,580,726); random-amplified polymorphic DNA (RAPD) (U.S. Pat. No. 55,665,572; Williams et al., *Nucleic Acids Res* 18: 6531–6535, 1990); simple-sequence repeat amplifications (U.S. Pat. Nos. 5,874,215; 5,576,180); consensus-sequence primed polymerase chain reaction (CP-PCR) method (U.S. Pat. No. 5,437,975); ligation chain reaction and the like.

As discussed above, it is not necessary to reduce the complexity of the starting nucleic acids when generating a diversity panel. However, many of the methods cited above are designed to reduce complexity. In one of the more commonly used methods (AFLP), complexity is reduced by digesting the DNA with a restriction enzyme, ligating adapters to the fragments, and then amplifying the fragments using a primer that corresponds to the adapter and restriction site sequences and contains one or more bases at the 3' end of the primer. If the primer has one extra base, on average, only $\frac{1}{16}$ of the fragments will amplify (only 1 in 4 fragments will have a complement to the extra base at one end of the fragment and 1 in 4 will have a complement at the other end of the fragment). In AFLP and many of the other amplification methods, the choice of primers will determine, at least in part, the fraction of the genome that is represented in the diversity panel. For example, more extra bases at the 3' end of the primer or primers used for amplification will result in a smaller fraction of the genome that will be amplified. Other parameters that can be altered to control the fraction of the represented genome include the DNA polymerase used, such as whether the enzyme can synthesize long stretches of nucleic acids, amplification reaction conditions, such as cycling times and temperatures, amount or type of cofactor in the reaction and the like. These and other parameters are known to those in the art and are widely used to affect the outcome of amplifications.

In certain embodiments, regions comprising insertion elements are amplified. Insertion elements are common in some organisms, may be mobile or immobilized, and many groups of such elements have been described. For example, transposable elements in plants (e.g., Ac, Ds, miniature inverted-repeat transposable elements (MITE) elements), insects (e.g., Drosophila P, gypsy), fungi (e.g., impala element, Scooter), animals (e.g., Tigger, mariner-like elements, B2 elements, long-interspersed elements (LINE)), bacteria, and the like, are well known and characterized. Amplification of these regions such that polymorphisms are revealed may be achieved with several different methods and primer pairs. For exemplary purposes, two methods are briefly described herein. In one method, a suitable primer pair comprises a primer that anneals to sequences that are conserved in the chosen family of insertion elements and the second primer anneals to genomic sequences flanking one side of the insertion. The sequence of the second primer may be chosen arbitrarily, such as for the arbitrarily-primed PCR methods cited above. Alternatively, the sequence can comprise (ordered from the 3' end) five (or more) arbitrarily chosen bases optionally linked to several or more bases in which all four bases are represented at each position followed by a defined sequence of at least 11 bases (e.g., at least 12 bases, at least 13 bases, at least 14 bases, and so on). The first round of amplification uses this primer pair and to obtain a greater degree of specificity, subsequent rounds of amplification use the first primer and for the second primer use the defined sequence. Variations on primer sequences, such as incorporating a restriction site and the like, and variation on methodology, such as performing nested PCR, are well known and commonly employed by those skilled in the art.

In another method, the nucleic acid molecules are digested first with a restriction enzyme, preferably one that does not cut within the insertion element. Adapters are ligated to the fragments, and the fragments are amplified with a primer pair in which the first primer anneals to sequences that are conserved in the chosen family of insertion elements and the second primer anneals to the adapter sequence. As for the methods above, variations on sequences and methodology can be employed within the context of this invention.

Non-amplification Methods

Alternatively, methods that do not rely upon amplification may be used to generate diversity panels. In the simplest form, restriction digestion using enzymes that recognize at least a six base sequence containing one or more degenerate bases, enzymes that cut infrequently, enzymes that cut DNA both 5' and 3' of the recognition sequence, enzymes that are sensitive or insensitive to methylation, or the like may be used. Other methods include primer-directed synthesis of DNA and the like.

Furthermore, amplification methods may also be combined with non-amplification methods. In an exemplary embodiment, fragments are generated by restriction enzyme digestion and ligated with an adapter sequence. These ligated fragments are then amplified with primers comprising the adapter sequence. Other exemplary embodiments are presented above.

Separation of Diversity Panel Products

As presented above, the discrete nucleotide sequences of the diversity panel are preferably separated prior to applying them to the array. In contrast, the discrete sequences of the diversity panel that are used to probe the array are preferably not separated. Separation may be achieved by any of a variety of methods. Such methods are known in the art and include, but are not limited to, cloning, gel electrophoresis, chromatography, e.g., HPLC, and dilution.

As an exemplary method, the diversity panel products are cloned into a suitable vector. Techniques for cloning are well known in the art (see e.g., Ausubel et al. Current Protocols in Molecular Biology, Greene Publishing, 1999). Briefly, if the products do not already have ends that are compatible for ligation into a chosen vector prepared by restriction digestion, the products need to be prepared. Typically, the products will either be digested with one or more appropriate restriction enzymes or treated with a DNA polymerase (e.g., *E. coli* DNA pol I) in the presence of all four dNTPs to produce blunt ends. The diversity panel products are then ligated to the cloning vector. Generally, the cloning vector is one that will replicate in bacteria. Many such vectors are commercially available (New England Biolabs, MA USA; Invitrogen, CA, USA; etc.) and include pBluescript, pET series vectors, pUC series vectors, and the like. Following ligation, the recombinants are transformed into a bacterial host, typically *E. coli*, and transformed bacteria are selected for or screened for.

Alternatively, the diversity panel products may be separated by gel electrophoresis, including capillary electrophoresis. Apparatuses for capillary electrophoresis are commercially available (e.g., Hewlett-Packard; CA USA; SpectruMedix, PA, USA). In general, separation by electrophoresis fractionates the nucleic acids by length, to an approximation. The separated diversity panel products are collected by means known in the art and transferred to the array substrate.

Other types of chromatography can also be employed. Such technologies include HPLC (high-performance liquid chromatography) and matched ion polynucleotide chromatography (Transgenomic, Inc. USA; U.S. Pat. Nos. 5,986,085; 5,997,742).

Another technique for separation, although less efficient that the other methods, is dilution of the diversity panel sample to a point where the sample drop to be applied to the array contains a discrete nucleotide molecule.

Application of Diversity Panels into an Addressable Array

Many types of materials, such as silicon wafers, borosilicate slides, microtiter plates, nitrocellulose or nylon membranes, may be used to form solid supports for the array, However, in practice, silicon wafers (readily available from the semiconductor industry) and borosilicate slides (e.g., microscope slides) are presently the preferred materials to serve as the solid support.

In certain embodiments, the nucleic acid molecule can be directly bound to the solid support or bound through a linker arm, which is typically positioned between the nucleic acid sequence and the solid support. A linker arm that increases the distance between the nucleic acid molecule and the substrate can increase hybridization efficiency. There are a number of ways to position a linker arm. In one common approach, the solid support is coated with a polymeric layer that provides linker arms with a lot of reactive ends/sites. A common example of this type is glass slides coated with polylysine (see, U.S. Pat. No. 5,667,976), which are commercially available. Alternatively, the linker arm may be synthesized as part of or conjugated to the nucleic acid molecule, and then this complex is bonded to the solid support. For example, one approach takes advantage of the extremely high affinity biotin-streptavidin interaction. The streptavidin-biotinylated reaction is stable enough to withstand stringent washing conditions and is sufficiently stable that it is not cleaved by laser pulses used in some detection systems, such as matrix-assisted laser desorption/ionization time of flight (MALDI-TOF) mass spectrometry. Therefore, streptavidin may be covalently attached to a solid support, and the nucleic acid molecule is labeled with a biotin group (or vice versa). The biotinylated nucleic acid molecule effectively sticks wherever it is placed on the streptavidin-covered support surface. In one version of this method, an amino-coated silicon wafer is reacted with the n-hydroxysuccinimido-ester of biotin and complexed with streptavidin. Biotinylated oligonucleotides are bound to the surface at a concentration of about 20 fmol DNA per $mm^2$.

Alternatively, one may directly bind DNA to the support using carbodiimides, for example. In one such method, the support is coated with hydrazide groups, then treated with carbodiimide. Carboxy-modified nucleic acid molecules are then coupled to the treated support. Epoxide-based chemistries are also being employed with amine modified oligonucleotides. Other chemistries for coupling nucleic acid molecules to solid substrates are known to those of skill in the art.

The nucleic acid molecules must be delivered to the substrate material. Because of the miniaturization of the arrays, delivery techniques must be capable of positioning very small amounts of liquids (e.g., less than 1 nanoliter) in very small regions (e.g., 100 μm diameter dots), very close to one another (e.g., 250 μm separation) and amenable to automation. Several techniques and apparatus are available to achieve such delivery. Among these are mechanical mechanisms (e.g., arrayers from GeneticMicroSystems, MA, USA) and ink-jet technology. Very fine pipets may also be used.

Other formats are also suitable within the context of this invention. For example, a 96-well format with fixation of the nucleic acids to a nitrocellulose or nylon membrane may also be employed.

After the nucleic acid molecules have been bound to the solid support, it is often essential to block reactive sites on the solid support that are not consumed in binding to the nucleic acid molecule. Otherwise, the probes will, to some extent, bind directly to the solid support itself, giving rise to so-called non-specific binding. Non-specific binding can defeat the ability to detect low levels of specific binding. A variety of effective blocking agents (e.g., milk powder, serum albumin or other proteins with free amine groups, polyvinylpyrrolidine) can be used and others are known to those skilled in the art (see, for example U.S. Pat. No. 5,994,065). The choice depends at least in part upon the binding chemistry.

Methods for Labeling and Detecting Nucleic Acid Probes

As discussed above, the nucleic acid molecules of the diversity panel that are used to probe the array are preferably directly detectable. Generally, a detectable molecule, also referred to herein as a label, will be incorporated or added to the diversity panel nucleic acid sequences. Many types of molecules can be used within the context of this invention. Such molecules include, but are not limited to, fluorochromes, chemiluminescent molecules, chromogenic molecules, radioactive molecules, mass spectometry tags, proteins, and the like. Other labels will be readily apparent to one skilled in the art. Indirect detection can also be used within the context of this invention. Proteins and other molecules are available that will bind to double-stranded DNA but not to single-stranded DNA. Thus, hybridization can be measured.

To maximize the use of the arrays, diversity panels that are used as probes may be mixed prior to hybridization as long as each diversity panel can be distinguished. Although there are various means to distinguish nucleic acids, in the simplest form, the products of each diversity panel in the mixture comprises a different detectable molecule. The number of diversity panels that can then be mixed and applied to the array at a single time is dependent on the number of distinguishable detectable molecules.

In one embodiment of this invention, diversity panel products are labeled with fluorochromes. A plethora of fluorochromes are commercially available or can be chemically synthesized. An extensive list of suitable fluorochromes, procedures for using them and detecting them is available in "Handbook of Fluorescent Probes and Research Chemicals" ($7^{th}$ Ed. Molecular Probes, Inc., Eugene, Oreg., USA, (www.probes.com)).

In an alternative embodiment, the nucleic acid molecules are directly or indirectly coupled to an enzyme. Following hybridization, a chromogenic substrate is applied and the colored product is detected by a camera, such as a charge-coupled camera. Examples of such enzymes include alkaline phosphatase, horseradish peroxidase and the like. The invention also provides methods of labeling nucleic acid molecules with cleavable mass spectrometry tags (CMST) (see for example, U.S. Pat. No. 60,279,890). After an assay is complete, and the uniquely CMST-labeled probes are distributed across the array, a laser beam is sequentially directed to each member of the array. The light from the laser beam both cleaves the unique tag from the tag-nucleic acid molecule conjugate and volatilizes it. The volatilized tag is directed into a mass spectrometer. Based on the mass spectrum of the tag and knowledge of how the tagged nucleotides were prepared, one can unambiguously identify the nucleic acid molecules to which the tag was attached (see, e.g., WO 9905319).

The nucleic acids can be labeled readily by any of a variety of techniques. When the diversity panel is generated by amplification, the nucleic acids can be labeled during the reaction by incorporation of a labeled dNTP or use of labeled amplification primer. If the amplification primers include a promoter for an RNA polymerase, a post-reaction labeling can be achieved by synthesizing RNA in the presence of labeled NTPs. Amplified fragments that were unlabeled during amplification or unamplified nucleic acid molecules can be labeled by one of a number of end labeling techniques or by a transcription method, such as nick-translation, random-primed DNA synthesis. Details of these methods are well known to one of skill in the art and are set out in methodology books (e.g., Ausubel et al., supra). Other types of labeling reactions are performed by denaturation of the nucleic acid molecules in the presence of a DNA-binding molecule, such as RecA, and subsequent hybridization under conditions that favor the formation of a stable RecA-incorporated DNA complex.

Hybridization to Arrays

The invention provides hybridization of a diversity panel to a diversity array, which is an addressable array containing products of diversity panels.

Typically, stringent hybridization and washing conditions are used for nucleic acid molecules over about 500 bp. Stringent hybridization conditions include a solution comprising about 1 M Na+ at 25° to 30° C. below the Tm; e.g., 5×SSPE, 0.5% SDS, at 65° C.; see, Ausubel, et al., *Current Protocols in Molecular Biology*, Greene Publishing, 1995; Sambrook et al., *Molecular Cloning: A Laboratory Manual*, Cold Spring Harbor Press, 1989). Tm is dependent on both the G+C content and the concentration of Na+. A formula to calculate the Tm of nucleic acid molecules greater than about 500 bp is $Tm=81.5+0.41(\%(G+C))-\log_{10}[Na+]$. Washing conditions are generally performed at least at equivalent stringency conditions as the hybridization. If the background levels are high, washing may be performed at higher stringency, such as around 15° C. below the Tm.

Low stringency hybridizations are performed at conditions approximately 40° C. below Tm, and are used for short fragments, e.g., less than about 500 bp. For fragments between about 100 and 500 bp, the Tm decreases about 1.5° C. for every fewer 50 bp than 500. For very small fragments, e.g., less than about 50 bp, a formula for calculating Tm is 2° C. for each AT pair and 4° C. for each GC pair. Very high stringency hybridizations are performed at conditions approximately 10° C. below Tm.

Hybridization conditions are tailored to the length and GC content of the oligonucleotide. Suitable hybridization conditions may be found in Sambrook et al., supra, Ausubel et al., supra, and furthermore hybridization solutions may contain additives such as tetramethylammonium chloride or other chaotropic reagents or hybotropic reagents to increase specificity of hybridization (see for example, PCT/US97/17413).

Detection and Analysis of Hybridization Products

Detection

Hybridization may be detected in a variety of ways and with a variety of equipment. In general, the methods may be categorized as those that rely upon detectable molecules incorporated into the diversity panels and those that rely upon measurable properties of double-stranded nucleic acids (i.e., hybridized nucleic acids) that distinguish them from single-stranded nucleic acids (i.e., unhybridized nucleic acids). The latter category of methods includes intercalation of dyes, such as ethidium bromide, into double-stranded nucleic acids, differential absorbance properties of double and single stranded nucleic acids, binding of proteins that preferentially bind double-stranded nucleic acids, and the like.

In preferred methods, the diversity panels applied to the addressable arrays are labeled with a detectable molecule. Examples of labels are discussed above. Following hybridization, some means of detecting a successful reaction must be addressed. The means of detection depend on the type of label used. For example, if a radioactive label is used, autoradiography or storage phosphor screens (Phosphorimager) are common methods of detection. Other systems, including chemiluminescent and fluorescent labels in conjunction with autoradiography, charge-coupled cameras or confocal microscopy, are part of an arsenal of detection systems.

An alternative detection system that can be used with radioactive, fluorescent or chemiluminescent labels is a CCD integrated silicon wafer. In this system, a charge-coupled device (CCD), designed to detect high energy beta particles or photons, is placed in direct contact with a silicon support for an array. Upon binding of the sample to the immobilized nucleic acids, a radioisotope decay product or photon is generated. Electron-hole pairs are generated in the silicon and then electrons are collected by the CCD.

An alternative detection system for fluorescent molecules is a lens based camera detecting one or more fluorescent labels. As mentioned above, these cameras include epifluorescent microscopes, confocal microscopes, and charge-coupled cameras. In the fluorescent systems, a laser excites a fluorescent label, the emitted light is collected through a bandpass filter, and the signal is detected by a photomultiplier tube that has electronics for counting photons.

Other labels are also amenable to use with either a lens-based camera or a CCD. For example, chemiluminescent labels or chromogenic substrates can be detected with a lens-based charge-coupled camera.

In some embodiments, the label is a cleavable mass-spectrometry tag. Such labels are then detected using a mass-spectrometer. Many detection systems are commercially available (e.g., Affymetrix, Santa Clara, Calif.). One skilled in the art is able to choose an appropriate detection means and equipment for the label used.

Analysis

A genotype of an organism is determined by the pattern of hybridization. Patterns can be expressed as presence or absence of hybridization, the degree of hybridization, or some combination of these. The simplest analysis is performed by determining the presence or absence of hybridization. When the complexity of the genome of the organism to be genotyped is greater than the complexity of the genome(s) represented on the array, the absence of hybridization conclusively signifies a polymorphism. When the complexity is less than on the array, the absence of hybridization can signify either a polymorphism or a lack of representation of those sequences in the probing diversity panel. The presence of hybridization, however, does not necessarily signify the absence of a polymorphism under either scenario. As described in more detail below, the pattern of hybridization is informative.

When the presence or absence of signal is assayed, each addressable area is queried for hybridization using a method appropriate to the label. For example, when fluorescent labels are used, such as Cy3 and Cy5, both green and red signals are assayed. When positive and negative controls are included on the array, signals are compared to the controls and each addressable area is assigned a value, e.g., 1 for detectable hybridization and 0 for no detectable hybridization. In general, a value of 1 is assigned for detection over a threshold level and 0 assigned for detection under a threshold level. It will be appreciated by those skilled in the art that detection of polymorphisms is based primarily on finding a binary distribution of signal values for any particular array feature when hybridized with multiple diversity panels. Preferably, the panels are the same as those used to create the diversity array (see Example 5). In case a diversity panel is generated from a heterozygote for a polymorphism, one will then detect a trimodal distribution. In such a case two threshold values are calculated, the: first threshold separates the "0" cluster (lack of hybridization) from the "0/1" cluster (heterozygote) and the second threshold separates the "0/1" cluster from the "1" cluster (hybridization present). Conventional statistical methods may be used to determine the threshold levels.

The genotype of the organism may then be expressed as a value for each addressable area. As an exemplary aid to understanding, if the addressable array is a 96-spot format (a grid of 8 rows (A–G)×12 columns (1–12)), and the value for hybridization is 1 and no detectable hybridization is 0, then visualization of a hypothetical genotype from one such grid may look like:

|   | 1 | 2 | 3 | 4 | 5 | 6 | 7 | 8 | 9 | 10 | 11 | 12 |
|---|---|---|---|---|---|---|---|---|---|----|----|----|
| A | 0 | 0 | 0 | 1 | 0 | 1 | 1 | 1 | 0 | 1  | 0  | 0  |
| B | 1 | 1 | 0 | 1 | 0 | 0 | 1 | 1 | 0 | 1  | 0  | 1  |
| C | 0 | 1 | 1 | 1 | 1 | 1 | 0 | 0 | 0 | 1  | 0  | 1  |
| D | 0 | 0 | 0 | 0 | 0 | 1 | 1 | 1 | 0 | 1  | 0  | 1  |
| E | 1 | 1 | 1 | 0 | 1 | 0 | 1 | 0 | 0 | 0  | 1  | 1  |
| F | 1 | 1 | 1 | 1 | 1 | 1 | 0 | 1 | 0 | 1  | 0  | 0  |
| G | 0 | 0 | 0 | 1 | 1 | 1 | 0 | 1 | 0 | 1  | 0  | 1  |
| H | 1 | 1 | 0 | 0 | 0 | 1 | 0 | 0 | 1 | 1  | 0  | 1  |

In a similar fashion, if the extent of hybridization is to be measured, then relative values are assigned to each addressable location. The relative values will generally be normalized to controls.

All data can be collected into database formats to facilitate comparisons as well as perform further analyses, such as construction of genotype trees.

Uses for Genotyping by Hybridization

As discussed and elaborated upon herein, genotyping by hybridization facilitates many different genetic studies, such as breeding of animals or plants, trait selection, introgression of traits, genetic disease diagnosis, forensic analysis, viral family detection, genomic mapping, determining origin of germplasm, establishing relatedness of germplasm, and the like.

Genotyping/Detection of Polymorphisms

As described above, this invention provides methods and compositions for establishing the genotype of an organism. Within the context of this invention, the genotype is expressed as presence/absence or extent of hybridization to individual nucleic acid molecules from two or more organisms. Until this invention, genotypes have been expressed in such ways as complete nucleotide sequence, explicit restriction fragment or amplified fragment lengths, a collection of genetic traits and the like. The present invention now allows genotypes to be written as it were by hybridization profiles.

One exemplary application of such genotyping is the determination of a number of individuals or strains within a species. In the world of plants, samples of a plant species are collected from around the world. Nucleic acids are extracted from these individuals. Genotypes of each individual are determined using the methods taught herein. Comparisons of the genotypes can reveal the relatedness of the individuals. Briefly, the closer the patterns of hybridization, the more related the individuals. In this way, for example gene flow can be documented.

In other systems, the gene flow or relatedness of viruses can be tracked. In this regard, the genotype of HIV infections is becoming crucial for predicting disease progression, selecting effective therapies, and the like. Other viruses or parasites, such as trypanosomes, that display extensive genotypic variation are useful candidates for the present invention.

Breeding programs for both plants and animals will benefit from this invention. For example, when there is a small population of rare animals that are being bred, it is believed important to interbreed unrelated individuals. Similarly, for plant breeding, it would be advantageous to characterize at the molecular level the diversity available to the plant breeder, so that he can choose the most appropriate individuals to work on before embarking on an extensive crossing and selection program. Most current means of determining relatedness are cumbersome, laborious and yield limited information. In contrast, the present invention allows high throughput and yields extensive information.

The present invention also provides methods for identifying polymorphisms. As discussed above, a polymorphism is identified by amplifying nucleic acids from two different organisms, preparing diversity panels from the two organisms, placing the diversity panel from one into an addressable array and hybridizing the array with the diversity panel of the other organism. When the fraction of the genome represented in the diversity panel on the array is the same or less than the fraction of the genome represented in the diversity panel in solution, a polymorphism is identified by the absence of hybridization. In a preferred embodiment, the arrayed diversity panel is cloned first and individual cloned molecules are placed into the array. When a polymorphism is identified it is then straightforward to isolate the clone and thus, the polymorphism. The nature of the polymorphism can be further characterized by sequence analysis, restriction site analysis, heteroduplexing, and the like.

This approach can be applied to the identification of a polymorphism genetically linked to a phenotypic trait: the strategy commonly known as Bulk Segregant Analysis can benefit from the present invention. Classically, a large number of individuals are scored for a particular trait or phenotype and each individual is placed in one of two possible categories. The DNA of individuals in each category is pooled and interrogated to identify markers specifically present in one of the two categories. A clear advantage of the present invention to perform this analysis is its parallel nature: in a single experiment, a large number of markers will be interrogated simultaneously. The chance of detecting a polymorphic marker distinguishing between the two categories is therefore higher.

Isolation of Polymorphism/Transgenic Plants

The nucleic acid molecule comprising a detected polymorphism is isolated using techniques known in the art. The nucleic acid molecule may be cloned in an appropriate vector if not already cloned. In turn, the clone may be mapped on the genome using conventional techniques or mapped to a collection of BAC or YAC clones. The nucleotide sequence may be determined as well.

In certain embodiments, the polymorphic nucleic acid molecule may be used to transform a host cell, either a plant or animal. Methods to make transgenic plants are known in the art. Depending upon the nature of the transgenic sequence it may be desirable to operatively link the sequence to a promoter that are active in plants. Such promoters may be constitutive, such as the 35S CaMV promoter, tissue-dependent, such as those active only in root tissues, stage-dependent, such as those active during embryogenesis, or the like. Examples of promoters are readily found in public databases (e.g., GenBank).

Following Polymorphisms Through Introgression/Back-Crossing

Introgression of specific alleles is a goal frequently pursued in plant breeding as well as laboratory animal breeding programs. The end product is a plant or animal nearly identical to the desired parent except for a specific region of the genome that is contributed by another individual. For example, the advent of mice strains with identical backgrounds but differing at the Major Histocompatibility Complex locus was instrumental in understanding the effect of MHC differences on organ transplantation. In crop development, a desirable trait, such as disease resistance, may be identified in a plant, but is generally introgressed into elite varieties that are better suited to the local environment, soil and climate or to consumer preferences than the original plant. The introgression is usually performed by repeated backcrosses of the new individual with the elite parent. During the introgression of the genes that account for the traits, means to follow that trait are necessary. In some cases, the trait may not be assayable in the field except under defined conditions (e.g., challenge with the pathogen). It is advantageous, however, to have a marker for the gene i.e. a polymorphism genetically linked to the desired trait, which can then be assayed to identify suitable plants for the breeding program. In order to accelerate the speed of the introgression process, it is also important to monitor that the rest of the genome is as similar as possible to the elite parent. In that regard, the determination of a genotype encompassing a large number of markers in parallel, provided by the present invention is a distinct advantage. The present invention provides the means to follow specific markers linked to a desirable traits, as well as genome-wide markers measuring the extent of reconversion of the genome, and allows for high throughput screening.

Constructing a Genetic Map; Discovering Important Genes through Association Studies The present invention provides the means to build rapidly a genetic map, even for organism for which little or no molecular data is available. Once the genotype of two individuals is determined according to the invention, the progeny arising from a cross between these individuals can be genotyped in a similar manner. Each individual from the progeny is genotyped. Commonly used softwares such as Mapmaker will then extract from the individual genotypes the co-segregation ratio between markers and calculate a linkage map of the markers. Determining rapidly the map position of a large number of markers allows breeders or geneticists to associate phenotypic data (such as qualitative or quantitative traits) with genetic data (such as molecular markers linked to the trait, markers for Quantitative Trait Loci and the like) and molecular data (such as DNA sequence associated with the markers, surrounding the markers, comprised between the markers, and the like). Association studies as described above are an important component of gene discovery and gene function identification in the agricultural as well as the medical field. With the rapid progress in genomics for an increasing number of plants and animals (for example the availability of the complete sequence of the human genome and the genome of *Arabidopsis thaliana*), this approach to gene discovery will become increasingly productive.

Varietal Identification

The fingerprint of an individual as determined by the present invention can be used to identify the individual unambiguously. Due to the parallel analysis of a large number of markers provided by the present invention, the identification is highly reliable and the fingerprinting process has a high throughput and a low cost. This reliable and cheap method for identifying plant or animal varieties is useful in a large range of activities: it will facilitate the detection by plant or animal breeders of unlawful copying of their registered varieties and it will facilitate quality control of identity preserved crops. Fingerprinting as provided by the present invention can also be used to identify the genotype of grains delivered by a producer, for example for the purpose of collecting royalties on the production of specific varieties.

The following examples are offered by way of illustration, and not by way of limitation.

EXAMPLES

Example 1
Generating a Diversity Panel from Rice Genomic DNA

Representative samples of rice germplasm are identified for genotyping. The samples are chosen solely for demonstration purposes and are chosen on the basis of other knowledge for being a diverse set of genotypes. This is done mostly through analyzing dendrograms based on sequence and/or molecular marker polymorphism in order to pick up members of separate groupings. Also representative genotypes can be identified as representatives of separate clusters if the results (like Principal Component Analysis) or clustering algorithms are available. Alternatively representative genotypes can be identified through single pass sequencing of rapidly evolving segment of the genome followed by similarity/dissimilarity analysis. DNAs from a sampling of genotypes representing genetic diversity of rice species (usually 10–15) are used to generate DNA diversity panels through a number of techniques, one of which is exemplified below.

In this Example, diversity panels are generated from genomic DNA prepared from 9 rice cultivars: Azucena, IR20, IR64, Italica, Karolina, Labelle, L203, Millin and Nipponbare. Three different restriction endonuclease (Table 1) digestions of the DNAs generate fragments, which are ligated with adapters, amplified and cloned. In this specific embodiment, primers for amplification are chosen such that the resulting products comprise a subset of the restriction fragments. With this method, complexity of the genome is reduced by 100 to 1000-fold compared to total genomic samples.

Genomic DNA is extracted from young seedlings (Murray and Thompson *Nucleic Acid Res.* 8: 4321–4326 (1980)). About 5 ng of DNA from each cultivar is digested at 37° C. for 1 hour with 2 units of restriction enzyme in a volume of 8 µl. Following digestion, 2 µl of ligase mixture is added, and the reaction is incubated at 37° C. for 3 hours. Ligase mixture comprises 0.2 µl T4 ligase (NewEngland Biolabs, MA), 0.2 µl 10×ligase buffer, 0.1 µl 100×BSA (NewEngland Biolabs, MA), 0.2 µl 50 mM ATP, 1.2 µl MilliQ (MQ) $H_2O$ and 0.1 µl of enzyme-specific adapter (Table 1) at 50 pmol/µl for MspI-specific adapter and 5 pmol/µl for EcoRI- and PstI-specific adapters.

After ligation, the mixture is diluted to 500 µl with MQ $H_2O$ and 2 µl is used as a template in a 50 µl amplification reaction with 2 units of RedTaq™ polymerase (Sigma Chemicals, St Louis, Mo., USA) and one of the primers (1.5 µl at 50 ng/µl) listed in Table 1. After incubation at 95° C. for 3 min the reactions are cycled 30 times: at 94° C. for 30 sec, 60° C. for 45 sec and 72° C. for 1 min. A final extension cycle is performed at 72° C. for 8 min.

TABLE 1

| Restriction enzyme | Adapter sequence | Primer sequence + selective bases at 3' end of primer |
|---|---|---|
| EcoRI | CTCGTAGACTGCGTACC (SEQ ID No 1) CATCGTACGCATGGTTAA (SEQ ID No2) | GACTGCGTACCAATTC-XXX (SEQ ID No 3) XXX = AAG, AGT, ACG, ATG |
| PstI | CACGATGGATCCAGTGCA (SEQ ID No 4) GACGTGCTACCTAGGTC (SEQ ID No5) | GATGGATCCAGTGCAG-X (SEQ ID No 6) X = T |
| MspI | GACTGTAGACTGCGATG (SEQ ID No 7) ACATCTGACGCTACGC (SEQ ID No 8) | GTAGACTGCGATGCGG-XX (SEQ ID No 9) XX = TG |

The amplified fragments are ligated into PCR2.1-TOPO vector using the TOPO™ cloning kit and transformed into heat-shock competent *E. coli* strain TOP10F' (Invitrogen, Carlsbad, Calif.) according to the manufacturer's instructions. Briefly, amplified products may be purified to reduce adapter and primer contamination. The ligation mixture, which contains approximately 2 µl of amplified products, is incubated for 5 min and terminated. About 2–2.5 µl of the ligation reaction is used to transform *E. coli*. Approximately 20–50 µl of the transformed *E. coli* is plated on L plates containing ampicillin for selection and X-gal for blue/white visualization to identify recombinant plasmids. Approximately 1000–2000 recombinants are typically isolated. This number represents a similar complexity as the diversity panels that are used for detecting polymorphisms.

Individual colonies that contain recombinant plasmids (white colonies) are transferred by toothpick into 20 µl of 10% glycerol. From each glycerol sample, a 5 µl aliquot is transferred to 45 µl of RedTaq™ amplification master mix containing 15 pmols each of Forward and Reverse M13 primers and 1.5 units of RedTaq™ polymerase. The reactions are incubated in microtiter plates for 5 min at 95° C. followed by 30 cycles of: 30 sec at 94° C., 30 sec at 54° C. and 1 minute at 72° C. (Thermowell™ 96 well plate Model M, Costar, Corning N.Y.) and 1 cycle of 72° C. for 5 min, followed by a hold at 4° C.

Following amplification the products are precipitated with one vol of isopropanol (100 µl) at room temperature. The plate is then centrifuged at 3200 rpm for 20 min at 4° C. All the liquid is removed, and the pellet is washed quickly with 100 µl of 70% EtOH. The plate is then further centrifuged for 10 min at 4° C. The EtOH is removed, and the plate is air dried. The pellet is resuspended at a concentration of about 20 ng/µl in MQ water, 3×SSC, or 1×SSC, 0.01% sarcosyl.

Example 2
Preparation of a Diversity Array

The amplified DNA inserts are transferred into 384-well plates (Genetix) and arrayed using a microarrayer (e.g., 417 microarrayer; Affymetrix, Palo Alto, Calif.) onto Polysine™ microscope slides (MenzelGlazer, Germany) or in-house polylysine-coated microscope slides. Arrays are made with six replicates per fragment. The average center to center spot spacing is 250 µm.

At least 1 day after arraying, slides are processed by hydration in 1×SSC, quick drying, blocking for 15 min in a solution of NaBrH$_4$/PBS (prepared by dissolving 1 g NaBrH$_4$ in 300 ml PBS, pH 7.0) (see also http://www.microarrays.org/protocols.html, Protocol for Post Processing Microarrays; June 2000, except that the succinate anhydride pyrolidone is replaced with NaBrH4 in PBS as the blocking solution). Slides are then dipped in boiling water for 30 sec to denature the DNA and followed by a 10 sec dip in 100% EtOH. Slides are dried by centrifugation at 1000 rpm in a slide rack on microtiter plate carriers for 1 minute.

Example 3
Determination of Fingerprints by Hybridization of a Labeled Diversity Panel to an Array For hybridization to a microarray prepared as taught in Example 3, a diversity panel of one or more specific genotypes is generated and labeled with a fluorescent dye. In a single hybridization experiment, a number of genotypes can be compared, the number being equal to number of labels that can be unequivocally detected and resolved. For example, an Affymetrix 418 scanner is equipped with "green" and "red" lasers, allowing for simultaneous analysis of two different samples.

Genomic DNA (200 ng–2 μg/μl) is cut with EcoRI and ligated to EcoRI adapters (1.5 μl of 5 pmoles/μl) using and excess of T4 ligase (40 units) for 3 hours at room temperature. For this step, 200 ng of DNA is sufficient, but 1 μg of DNA provides sufficient material for a number of hybridizations. Following ligation, the mixture is purified on a Qiagen column.

An amplification reaction contains 2.5 units RedTaq™ (Sigma, St. Louis, Mo. USA), 1–5 μl of ligated genomic DNA from above, 10 μl 10×buffer (10×buffer contains 500 mM KCl, 1 M Tris-HCl (pH 8.8), 0.1% Triton X-100, 15 mM MgCl$_2$), 10 μl of 2 mM dNTPs, and 1 μl of 20 pmol/μl primers. Because the DNA fragments are ligated with an adapter a single primer identical to one strand of the adapter is used with one or more additional bases added to the 5' end. In some experiments a mix of primers is used that are identical to one strand of the adapter but have one or more additional bases at the 3' end of the primer. Such a mix serves to limit the complexity of the resulting fingerprint.

Amplification conditions are 1 cycle of 95° C. for 2 min, 30 cycles of 94° C. for 30 sec, 54° C. for 30 sec, 72° C. for 1.1 min, 1 cycle of 72° C. for 5 min and hold at 4° C. Amplification products are purified using Qiagen Quick PCR™ purification columns to remove the dNTPs, which otherwise will affect the labeling steps.

Amplified material is labeled by incorporating dUTP-Cy3 or dUTP-Cy5 using a random priming method. In this method, up to 11 μl of DNA in MQ water is mixed with 2 μl of *E. coli* DNA Pol I and 1 μl of 3 μg/μl hexanucleotides in 10 mM Tris-HCl (pH7.5), 5 mM MgCl$_2$ and 7.5 mM dithiothreitol,. The mixture is boiled for 2 min and snap-cooled on ice for 5 min. The following ingredients are then added: 2 μl of 2 mM each dATP, dGTP, dCTP and 90 μM dTTP, 1–2 μl of dUTP-Cy3 or dUTP-Cy5, and 1 μl (5 units) *E. coli* pol I (large fragment). The reaction mixture is incubated for 3 hours at 37° C. and terminated by the addition of 50 mM EDTA. The two labeling reactions (Cy3 and Cy5) are pooled and purified together using Qiagen columns according to the manufacturer's recommendations, except that one extra wash using 0.5 ml wash buffer is performed. The labeled nucleic acid molecules are eluted in ~30 μl of water.

Alternatively, amplified material can be labeled using a Deca-random-prime DNA labeling kit from Fermentas (Vilnius). When this kit is used, minor deviations from the manufacturer's instructions are used, specifically the reaction volume is reduced to 5 μl, the time increased to 1 hour and 0.4 μl of 1 mM Cy3-dUTP or Cy5-dUTP is used instead of $^{32}$P-dNTPs. Probes are not purified for hybridization.

Prior to hybridization, 5 μl of the labeled material is mixed with 2 μl of 20 mg/ml herring sperm DNA which is dissolved in Express Hybridization™ buffer (Clontech, Palo Alto, Calif., USA), and the mixture is denatured at 96° C. for 3 min. The denatured probes are mixed with 10 to 15 μl of ExpressHyb hybridization solution, pipetted directly onto the microarray surface and covered with a glass cover slip (24 mm×24 mm Mediglass, Australia). Slides are then quickly placed into a homemade humidification chamber in a 65° C. water bath for overnight hybridization.

After hybridization, the coverslips are removed, and the slides are rinsed in 1×SSC with 0.1% SDS for 5 min; 1×SSC for 2 min; 0.2×SSC for 2 min; and 0.02×SSC for 20 sec; all solutions are at room temperature. Slides are quickly dried by centrifugation at 1000 rpm in a slide rack on microtiter plate carriers for 1 min.

The intensity of fluorescence at each spot is measured by scanning the slide with an array reader (for example Affymetrix 418 microarray scanner). Fluorescence is read using scanner settings appropriate for the fluorescent dyes used in labeling reaction. For example: for Cy3 dye, the green laser is set to PMT 60 and laser power at 100%, and for Cy5 the red laser is set to PMT 90 and laser power at 100%. Scanning conditions are adjusted if necessary.

Identification of polymorphic clones may be made by visual inspection of a graphic file representing an overlay of scanning results for two genotypes to be compared. An overlay can be a result of single hybridization or, alternatively scans from independent hybridizations can be overlayed. Polymorphic clones may be identified as those hybridizing to only one of the two samples compared. Numerous statistical methods are available to facilitate conversion of signal intensities into binary (presence/absence) characters. Large populations of genotypes can be analyzed in pairs to develop similarity/dissimilarity measures matrix for the whole population.

In certain experiments, spot signal intensities are analyzed by Scanalyse ver. 2.44 (Stanford University) as well as GenePix Pro v. 3 (Axon Instruments) and GMS Pathways (Affymetrix v. Beta). The outputs of these image analysis programs are further analyzed using a program developed for Mathcad v. 8.

Figures 5A, 5B:
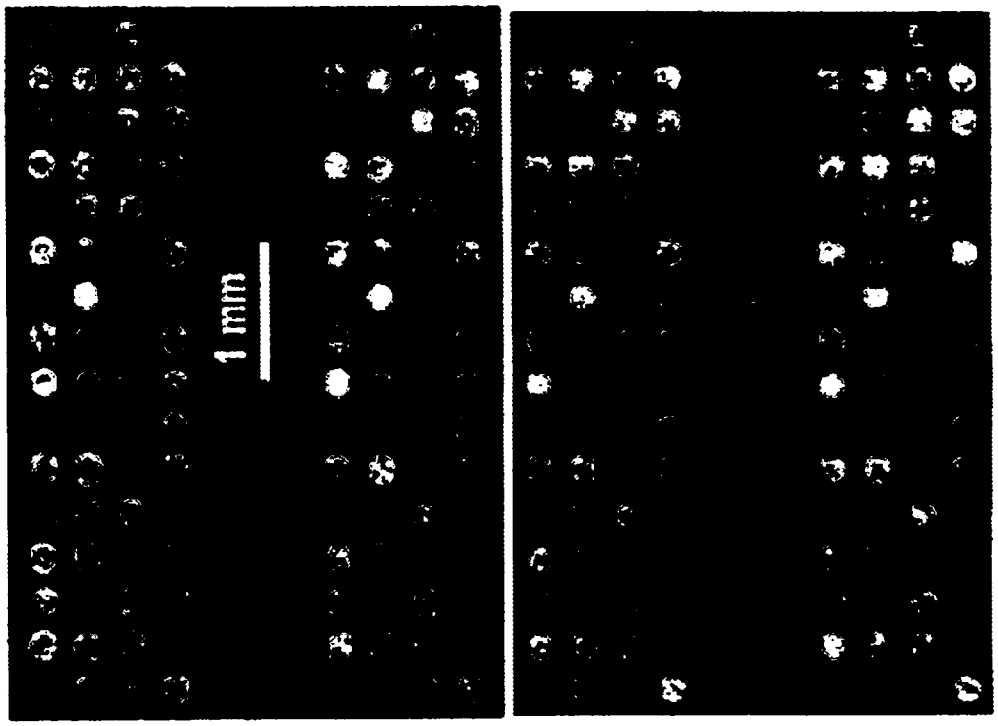
FIGS. 5A and 5B show hybridization of Cy3-labeled IR20 diversity panel and Cy5-labeled Millin diversity panel (FIG. 5A) and Cy3-labeled IR64 diversity panel and Cy5-labeled Millin diversity panel (FIG. 5B) to duplicate addressable arrays of a mixture of diversity panels.
Figure 6A:
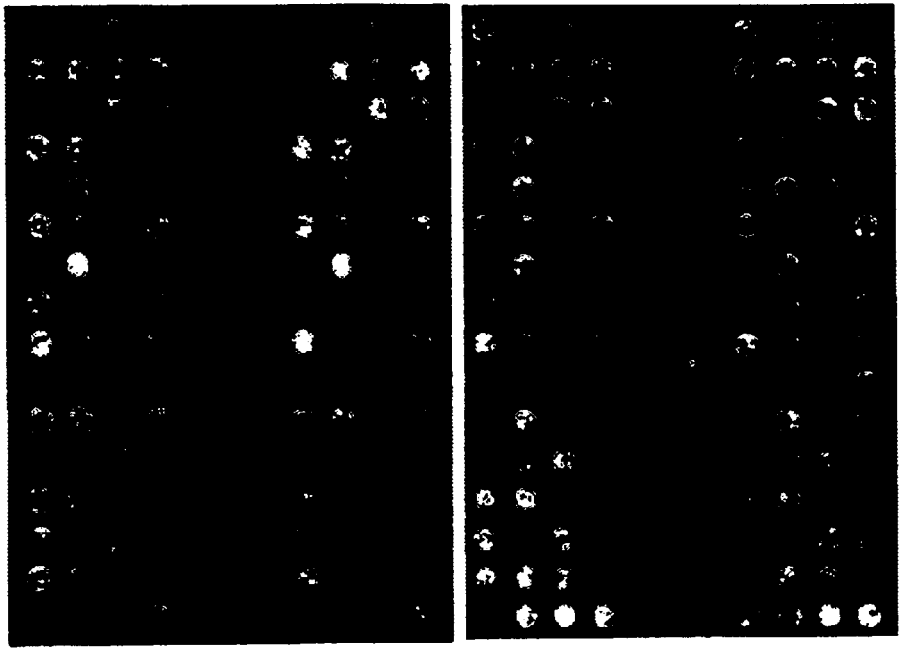

Representative examples of outputs can be seen in FIGS. 5 and 6.

Example 4
Comparison of Two Samples on a Single Array

In this example, fingerprints of rice cultivars are determined by hybridization of labeled diversity panels to a diversity array comprising a diversity panels generated from a mixture of 9 rice genomes. A schematic of this type of experiment are compared on a single array as exemplified in FIG. 1B.

The diversity panels are generated using 9 cultivars of rice (3 indica and 6 japonica types). Several panels are constructed using the pair-wise combination of restriction enzymes and primers described in Table 1. The resulting fragments in the diversity panel range from 0.3 to 2.4 kb with an average insert size of around 1 kb. In analysis of the fingerprints from hybridization data, an array feature or element is scored when the signal is at least 3 times the level of local background for the vector control (TOPO). At least 90% of array elements are scored for the panels analyzed in these examples. Furthermore, this value is reached without purification of amplification products.

Figure 2A:
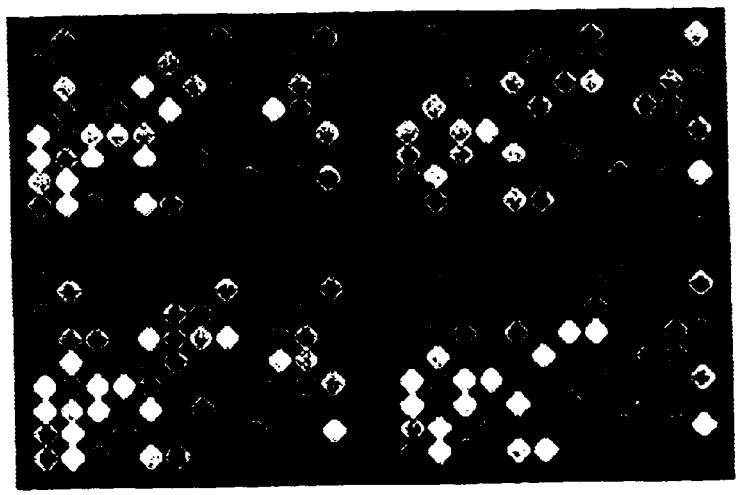
FIGS. 2A and 2B show differences between fingerprints of two rice cultivars, IR64 and Millin. (A) Synthetic array image of 96 spots printed 4 times from an EcoRI-generated diversity panel. The rice cultivars IR64 and Millin are labeled with Cy3-green and Cy5-red respectively. (B) Histogram of green to red normalized signal intensity ratios shows tri-modal distribution. The majority of the array features show signal intensity ratios are around 1 indicating equal hybridization intensity for Millin and IR64. The green and red "tails" are seen at signal intensity ratios above 2.9 indicate features of the diversity panel that differentiate IR64 and Millin DNA.
Figure 2B:
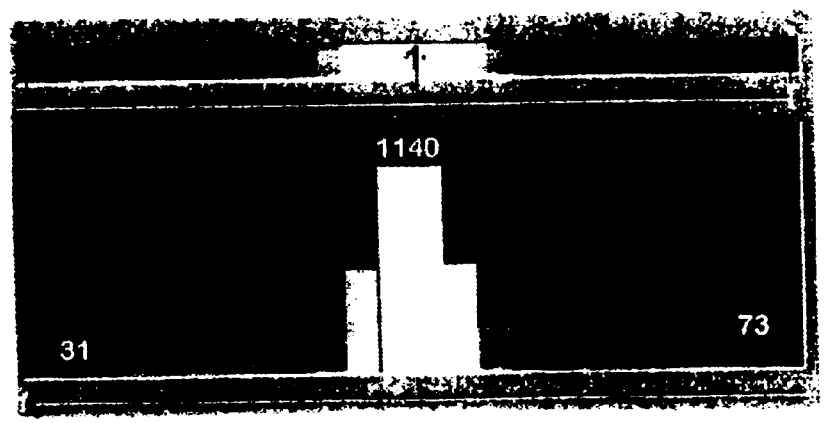

Fingerprints for four rice cultivars (Bala, Millin, IR64 and IR20) are determined by hybridization of a diversity panel from each cultivar to the EcoRI-generated diversity panel of the 9 mixed rice genomes. Pairs of the rice cultivars (e.g., Millin and IR64; Bala and IR20) are labeled with two different dyes for ease of detection. A comparison between Millin (sub-genomic sample labeled with Cy5 dye) and IR64 (sub-genomic sample labeled with Cy3 dye) shows a high level of variation in signal intensity (brightness of array features) and Cy3/Cy5 signal ratios among array elements (FIG. 2A). Furthermore, a histogram showing green to red channel normalized signal intensity ratios (FIG. 2B) shows a tri-modal distribution. The majority of the array features cluster around a ratio of 1, indicating equal signal intensity for Millin and IR64 samples (monomorphic features). The red and green "tails" represent the groups of "polymorphic" spots.

Several DNA fragments identified in this analysis as potentially polymorphic between Millin and IR64 (with the red/green ratio above 2.5) are used as probes on genomic and sub-genomic Southern blots (FIG. 3). These candidate clones are labeled and hybridized to blots of diversity panels and genomic DNA from four rice genotypes analyzed most extensively through microarray hybridization method. Genomic DNA (2 $\mu$g) is cut with EcoRI, resolved in 0.8% agarose gel and transferred to nylon membranes (FIG. 3A). Diversity panels are prepared as described above, resolved using 1.5% agarose gel and transferred to positively charged nylon membrane (Boehringer Mannheim) (FIG. 3B). Amplified inserts from the same clone DNA that is arrayed are labeled with $^{32}$P using the large fragment (Klenow) of E. coli DNA pol I. The radioactive labeled probes are hybridized with blots of diversity panels and EcoRI-digested genomic DNA.

FIG. 3 (left panels) shows the results of hybridization of candidate clone F4, which is polymorphic by fingerprint analysis when a diversity panel of Millin is tested against diversity panels of Bala, IR20 and IR64. Thus, in FIG. 3B, F4 hybridizes strongly with Millin diversity panel (lane 2), whereas F4 does not detectably hybridize to Bala (lane 1), IR64 (lane 3) and IR20 (lane 4) diversity panels. Hybridization of clone F4 to genomic DNA (FIG. 3A), which was digested with EcoRI, the same enzyme as used to generate the diversity panel, reveals a fragment about 1.6 kb in Millin DNA (lane 2) and a 2.3 kb fragment in the remaining DNAs. This restriction fragment size difference accounts for the presence (Millin) or absence (remaining three genotypes) of a signal apparent on the diversity panel Southern (FIG. 3B). In this example a Restriction Fragment Length Polymorphism (RFLP) in genomic DNA was converted to the presence/absence polymorphism in sub-genomic samples that can be identified in a highly parallel fashion using the DNA microarray platform.

A second candidate polymorphic fragment, clone F8, also shows polymorphism on Southern analysis. In this case, a smaller EcoRI fragment (1.3 kb) is detected in Millin and Bala DNA (lanes 1 and 2), whereas both IR20 and IR64 DNA display a 1.5 kb fragment (lanes 3 and 4) (FIG. 3A). However, while on the genomic Southern the band intensities are similar, in the diversity panel Southern, the hybridization strength to IR64 and IR20 are much weaker compared to the Millin and Bala bands. The difference in the abundance of specific amplified material in the diversity panel translates into easily detectable polymorphism in microarray experiment when Millin is contrasted with IR20 or IR64. In this case, an RFLP is converted to a quantitative polymorphism detected by signal intensity differences between Millin and IR64 sub-genomic samples on the array.

Figure 4:
FIG. 4 shows the result of hybridization of monomorphic clone F11 to EcoRI-digested genomic DNA from strains Millin, Bala, IR20, and IR64.

One additional clone, F11, is characterized in this example. F11 scores as monomorphic when analyzed against four rice cultivars, i.e., approximately equal signal intensity is observed for this clone when the array containing it is probed against any of the four labeled diversity panels. F11 is also tested as a probe against a Southern blot of diversity panels from these genotypes. FIG. 4 shows clearly that similar size (and abundance) products hybridize with the F11 probe in all four genotypes.

This EcoRI-generated diversity panel is also used to determine the minimal amount of DNA required for generation of reproducible diversity panels. Four different amounts of adapter ligation products, from 0.2 ng to 12.5 ng, are used for amplification of four genotypes (Bala, Millin, IR64 and IR20) and hybridization results are analyzed for polymorphisms. All genotypes are scored reproducibly as either present (1) or absent (0) for 14 elements identified as polymorphic at the four DNA amount levels (data not shown).

Example 5

Identification of Array Elements as Polymorphic or Non-Polymorphic

In order to identify the elements of the array that represent polymorphic DNA fragments all nine rice cultivars used for Diversity panel generation are analyzed on duplicate slides as described in these Examples. The spot intensities normalization, data transformation (to obtain near log-normal distribution) and polymorphic spot detection are achieved using the Mathcad 8.0. The program calculates the value (marked as "x" on each curve) best separating the two clusters of low and high signal ratios, respectively, and classifies each sample analyzed at the particular polymorphic feature as either 0 (low value cluster) or 1 (high value cluster). A table of binary scores is created automatically for all the samples and the polymorphic array. Typical distributions of normalized ratios of signal intensities (the signal for MspI sub-genomic sample labeled with Cy3 divided by the signal for Topo vector control labeled with Cy5) for four examples of non-polymorphic (FIG. 7A) and polymorphic (FIG. 7B) spots are presented. For all non-polymorphic spots the ratios of signal intensities show a monomodal distribution across 18 slides (9 cultivars×2 slides per cultivar). The polymorphic spots (FIG. 7B) show a clear bimodal distribution for the log transformed signal ratios.

Figure 7A:
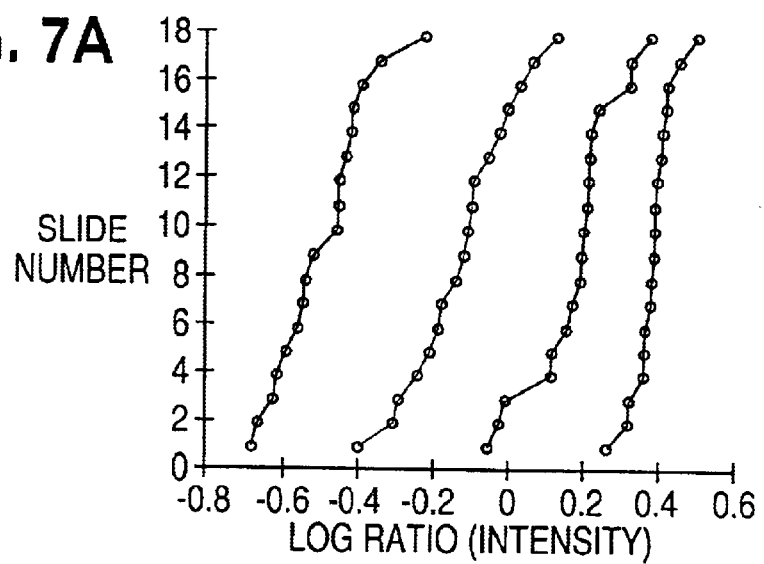
FIGS. 7A, 7B, and 7C show cumulative distribution functions for non-polymorphic fragments (A), polymorphic fragments (B), and a reference fragment (C). (A) Cumulative distribution function of log transformed normalized signal ratios for 4 different non-polymorphic spots across 18 different slides. Classification as non-polymorphic is based on the monomodal distribution of the ratios across the 18 slides. (B) Cumulative distribution function of log transformed normalized signal ratios for 4 different polymorphic spots across 18 different slides. Classification as polymorphic is based on a clear bimodal distribution across the 18 slides. The algorithm calculates the best value for separation of the high (value of 1) and low (value of 0) clusters shown as a cross on the curves. (C) A cumulative distribution function of the normalized log intensity values of a reference fragment (TOPO) across 18 slides adjusted to have equal medians. Each slide has 2304 spots (384 spots printed 6 times). One curve is shown in red; it is the result of a technical problem in a single experiment.
Figure 7B:
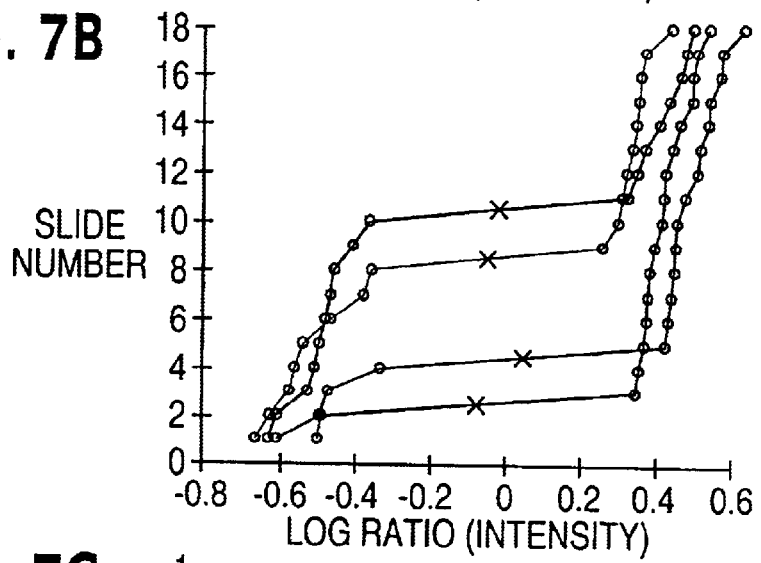
Figure 7C:
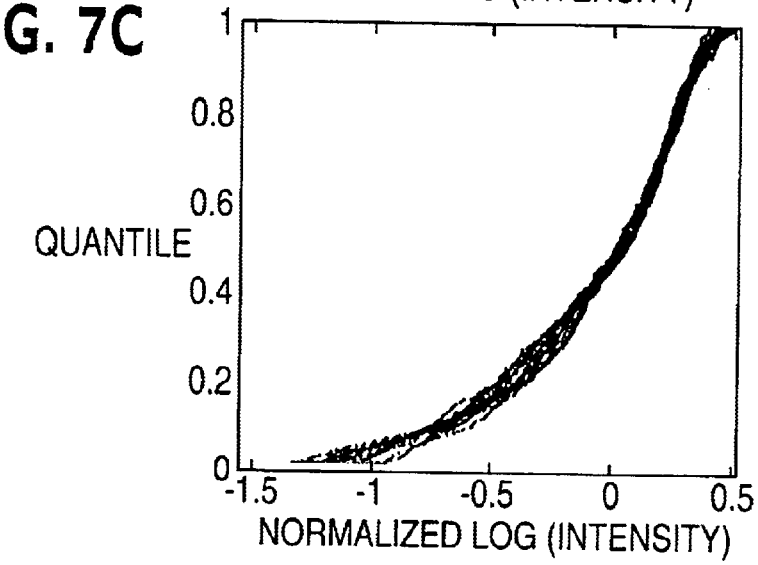

In FIG. 7A it is apparent that the range of ratios is larger for spots with an average ratio value below zero (in which the signal from the sub-genomic sample is weaker than the Topo control signal). Distribution of the ratios for all 384 features of the MspI panel for the same set of 18 slides (FIG. 7C) shows more variation between slides at lower values (especially below −0.2). The presence of a different number of "positive" spots among genotypes tested is likely to be one of the sources of the between slide variation. However, since the proportion of the polymorphic spots is relatively low this result most likely indicates that array features that hybridize weakly to the sub-genomic sample (around 30% of the total number) are more influenced by the noise in our system compared to the more strongly hybridizing ones.

The number of array features found as polymorphic among nine rice cultivars is 50 (14.5% of scored spots) for the MspI diversity panel. Apart from providing an estimate of polymorphism level detectable by this system, identification of polymorphic features allows assessment of the level of redundancy among them. DNA fragments representing array elements displaying the same pattern of polymorphism (same binary scoring) among the nine rice cultivars are resolved on an agarose gel. DNA fragments with the same apparent mobility are scored as repeats (FIG. 8). The analysis revealed that 50 polymorphic spots represented 28 unique clones of which most (20) had just one copy in the MspI panel of almost 400 clones. Based on the average MspI fragment size (under 1 kb), the rice genome size of 430 Mb, and 256-fold complexity reduction due to the amplification primers used having two selective bases ($\frac{1}{16} \times \frac{1}{16}$), over 1000 unique fragments are expected in the MspI diversity panel, even if less than 50% of the fragments amplified efficiently. The presence of mostly unique clones among polymorphic spots evidences that this invention can analyze fairly complex samples.

Analysis of diversity panels roughly 16 times more complex (using an amplification primer with a single selective base) indicates that through minor modification of the assay sensitivity (e.g. spotted DNA concentration, diversity panel labeling and scanning efficiency, etc.) a comprehensive genome scan can be achieved using the present invention.

Example 6

Using Diversity Arrays to Determine the Relatedness of Genomes

Figure 9A:
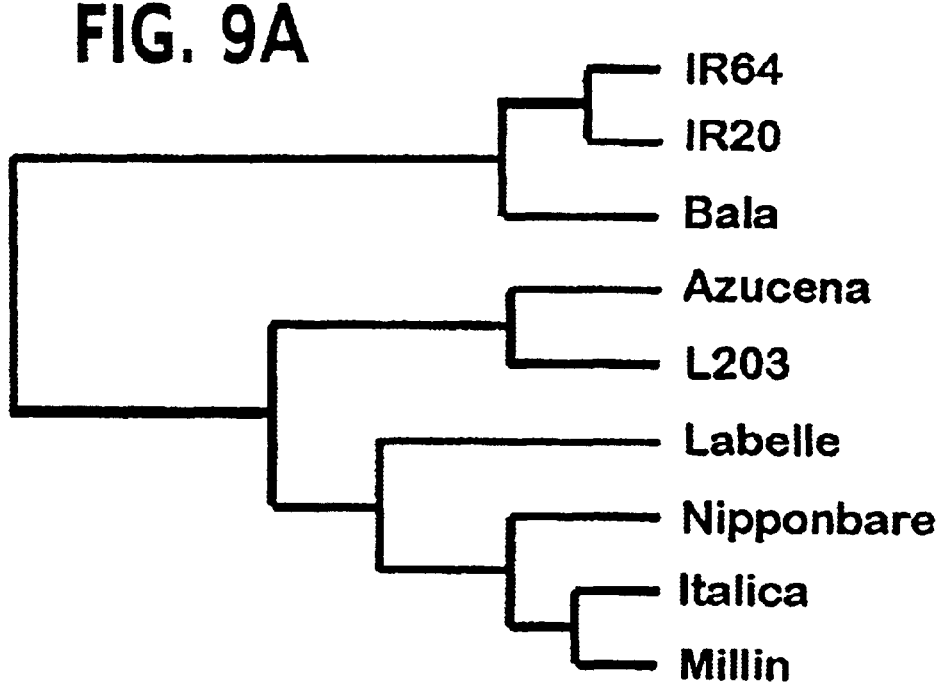
Figure 9B:
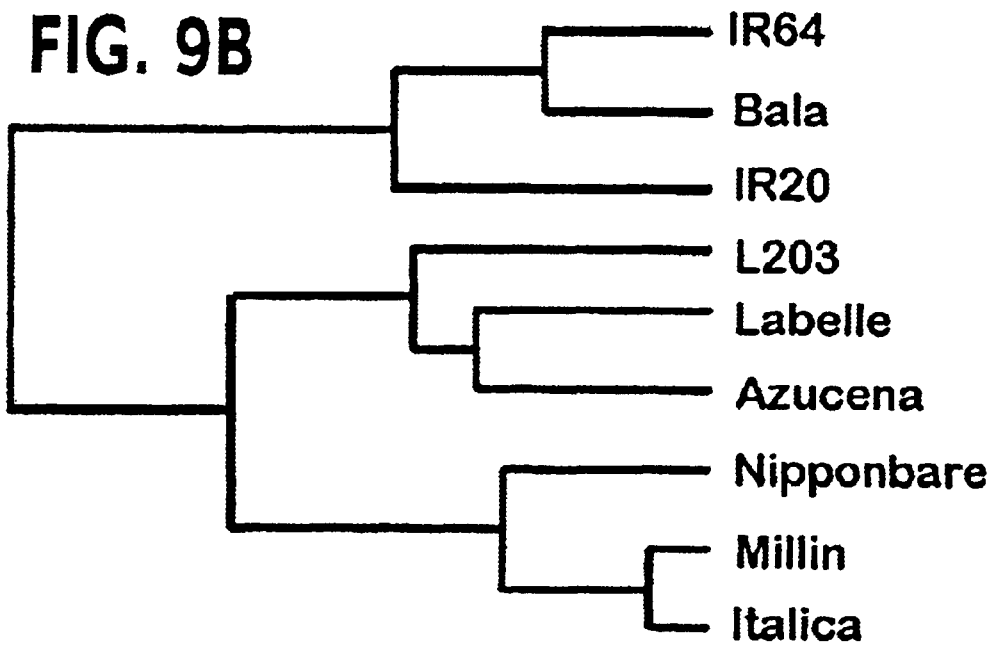

The binary scoring table for the 28 unique polymorphic features is used to calculate the distances between the cultivars. A distance table is used to produce dendrograms showing the relatedness of the cultivars. Binary scoring tables of 28 unique features from MspI and 28 from PstI are clustered by Cluster program (Stanford University) using similarity metric setting of correlation uncentered and presented by treeview (Stanford University). Differentiation among the cultivars analyzed and separation between japonica and indica types is apparent in both dendrograms. FIG. 9A shows the separation between indica and japonica rice cultivar classes based on fingerprints established from using the MspI diversity panel. Similar results are found using the PstI-generated diversity panel (FIG. 9B).

Example 7

Polymorphisms are Inherited in a Mendelian Fashion

In order to verify that the polymorphisms detected by this system behaved as Mendelian markers doubled haploid (DH) lines developed from the cross between IR64 and Azucena (REF) are used for genetic mapping. All 40 polymorphisms segregating in the DH lines population are successfully mapped on the microsatellite-based framework without any apparent clustering of the new markers.

Example 8

Fingerprinting Using a Complex Mixture of Diversity Panels

Figure 10A:
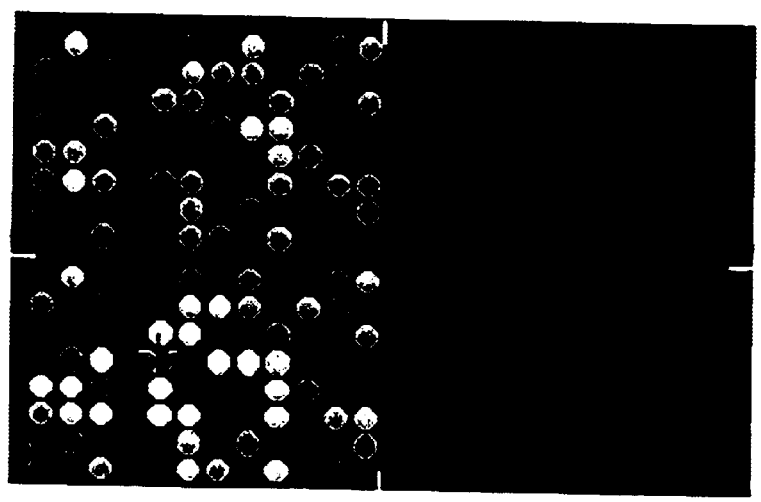
Figure 10B:
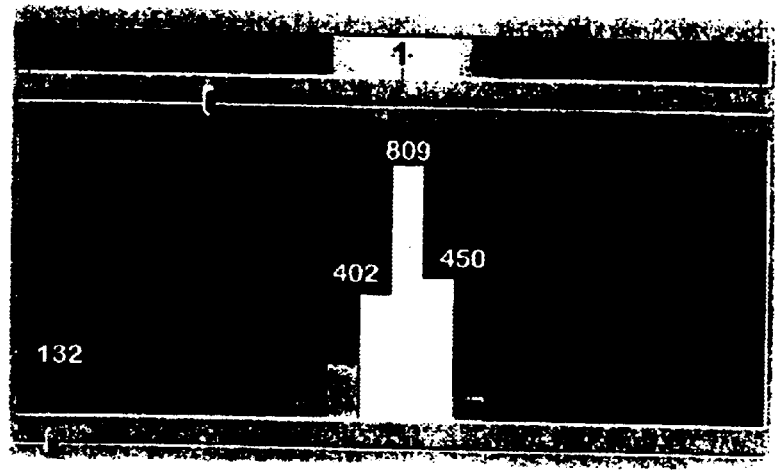

In this example, complex DNA samples are analyzed to demonstrate that minor amounts of a genome are detectable. DNA fragments from diversity panels developed from 8 species are arrayed on the same slide. The mix included rice and 7 species of micro organisms. This composite panel is then used as a target for hybridization with a diversity panel comprising sub-genomic samples from rice with or without a DNA admixture from microorganisms. In one example, the diversity panel from rice cultivar Millin, which is labeled with Cy5 dye, is hybridized to the composite panel together with a mixture (at 10:1 DNA ratio) of Millin and Enterobacter sp (closest *Buttiauxella agrestis*) (Sproer, C. et al., 1999) diversity panels labeled with Cy3 dye (FIG. 10). The left part of the panel (FIG. 10A), containing rice-derived features, shows mostly yellow spots, indicating a similar level of hybridization signal for the "pure" Millin diversity panel as for the Millin mixed with Enterobacter diversity panels. This observation is confirmed by the histogram of signal ratio distribution (FIG. 10B) indicating a lack of rice derived features with ratio larger than 2.5. At the same time, there is a clear pattern of strongly "green" features (ratios larger than 2.5) located exclusively to the addresses of the Enterobacter-derived features. There is no significant signal detected at other microorganism-derived spots on the composite panel, even with closely related species as determined by 16S sequence homology analysis.

Example 9

Efficient Detection of DNA Polymorphisms in the Barley Genome

In this example, diversity arrays are used to identify polymorphisms in the barley genome, which is more than 10 fold larger than the rice genome. Barley diversity panels are generated using DNA from 3 barley cultivars: Steptoe, Morex, Harrington, and from *Hordeum spontaneum* (wild barley) accession OSU 15. Diversity panels are constructed according to the Examples above, except that the restriction enzyme PstI is used to generate panels having complexities 100 to 1000 fold less than total genomic samples (below). Varying complexities of panels are achieved by the choice of primers used in amplification. Fragments from the panels are cloned, and inserts are individually amplified from bacterial colonies before arraying on glass slides.

Genomic DNA is extracted from seedlings of various cultivars. Genomic DNA (50 ng) is digested at 37° C. for 1 hour with 2 units of PstI restriction enzyme in a volume of 8 µl. After digestion, 2 µl of ligase mixture is added. Ligase mixture consists of 0.2 µl T4 ligase (New England Biolabs, USA), 0.2 µl 10×ligase buffer, 0.1 µl 100×BSA (New England Biolabs, USA), 0.2 µl 5 mM ATP, 1.2 µl MilliQ (MQ) H$_2$O and 0.1 µl (5 pmoles) of PstI adapter:

5'-CACGATGGATCCAGTGCA-3' (SEQ ID No: 10) and
5'-CTGGATCCATCGTGCAG-3' (SEQ ID No: 11).

After ligation for 3 hours at 37° C., the mixture is diluted to 500 µl with MQ H$_2$O. 2 µl of the diluted ligated DNA is used as template from amplification in a 50 µl reaction using 2 units of RedTaq™ polymerase (Sigma, USA). The sequence of the amplification primers are either GATGGATCCAGTGCAG (SEQ ID No: 12) or GATGGATCCAGTGCAG-X (SEQ ID No: 13) where X is A, C, G or T. Single primer for SEQ ID No: 12 or a combination of primers of SEQ ID No: 13 are used in amplification to achieve various levels of complexity reduction. Amplification parameters are 1 cycle at 95° C. for 3 min, 30 cycles at 94° C. for 30 sec, 60° C. for 45 sec, 72° C. for 1 min, followed by 1 cycle at 72° C. for 8 min. The amplification products are cloned, amplified and arrayed according to methods in Examples 1 and 2.

Diversity panels are prepared as above from cultivars Morex and Steptoe. The amplification primer used has the sequence 5'-GATGGATCCAGTGCAG-3' (SEQ ID No: 14). The amplification products are labeled with fluorescent dyes (Cy3 for the Morex diversity panel and Cy5 for the Steptoe diversity panel) and the hybridized to slides containing the PstI diversity panels from above. Hybridization, washing, image capture and analysis is done according to methods described in Examples 3 and 4. FIG. 11 shows a fragment of the array with polymorphic array features indicated. Depending on the PCR primer used the frequency of polymorphic array features detected between Morex and Steptoe varied from 10–15%.

Example 10
Detecting Polymorphisms in the Mouse Genome using cDNA Diversity Arrays In this example, diversity arrays prepared from cDNA are used for genotyping analysis. For any organism, cDNA or EST sequences may be used as a diversity panel that can be arrayed and used to establish genotypes.

As an example of this approach, a cDNA library from multiple mouse strains and tissues is arrayed on glass slides (>5000 independent cDNA clones per slide). Arraying and slide processing is done as in Example 2. Diversity panels for probing the cDNA are prepared according to the methods taught in the examples from two mouse strains, strain C57Bl/6 and strain NOD K. Briefly, 0.1 microgram of genomic DNA is digested by MspI restriction endonuclease, an adapter with an MspI-compatible end is ligated to the restriction fragments, and the fragments are amplified using an adapter-specific primer. Amplification products are labeled using fluorescent dyes (Cy3 and Cy5) and hybridized to the cDNA diversity arrays using Quick Hyb™ buffer (Clonetech). Hybridization, washing, image capture and analysis is carried out as described in Examples 4–6.

When a diversity panel generated from strain C57Bl/6 that is labeled with Cy3 is hybridized along with a similarly generated representation from strain NOD K that is labeled with Cy5 to the cDNA diversity array, about 25% (1410/5472) of cDNA array features show detectable signal. Among these with detectable signal 144 (10.2%) have a ratio of Cy3/Cy5 signal that is $\geq 3.0$ or $\leq 0.33$, indicating polymorphic regions. Because the arrayed nucleic acids are cDNAs, these polymorphic features are markers not only for a specific area of the genome but also for a specific gene. A section of the cDNA diversity array showing non-polymorphic and polymorphic features is presented in FIG. 12.

Example 11
Diversity Array Analysis Using cDNA Arrays and Diversity Panels Generated without Amplification In this example, the diversity panel is generated from genomic DNA by a method that does not utilize amplification. Instead, the DNA is digested with a restriction enzyme and a range of lengths of the restriction fragments are chosen and isolated. The panel is then labeled with fluorescent dye and hybridized along with a similarly prepared diversity panel from a second sample to a diversity array comprising a large collection of cDNAs.

As in the example above, mouse cDNA diversity arrays are prepared using 4000 cDNA clones. Diversity panels are created from two mouse inbred strains, NOD K and C57Bl/6 by MspI digestion of 10 µg of total genomic DNA. Digested DNA is electrophoresed in a 2.0% agarose gel, and a section of the gel containing fragments from 300 bp to 700 bp is isolated. The DNA is extracted from the agarose and purified using a gel extraction kit (Qiagen). The purified DNA is labeled with Cy3 (strain C57Bl/6) or Cy5 dye (strain NOD K), respectively, using a method described in Example 3. Hybridization, washing and image analysis is done using techniques described in Examples 4 and 5. Polymorphic array features are identified as those with Cy3/Cy5 signal ratio $\geq 3.0$ or $\leq 0.33$. In this particular contrast 9% of the array features are identified as polymorphic.

Example 12
Detecting Polymorphisms Due to Transposon Insertions in Rice

Diversity array technology is also suitable for detecting polymorphisms resulting from insertions in the genome. Since transposable elements are among the primary source of this type of DNA polymorphism, amplification of transposons is used as a method of generating diversity panels for probing rice diversity arrays. This example presents polymorphisms due to the transposon, called Stowaway (Bureau et al., *Proc Natl Acad Sci USA* 93: 8524–8529, 1996), which is a member of the MITE (Miniature Inverted Repeat Transposable Elements) class of mobile elements. Diversity arrays are generated by amplifying sequences that direct adjoin the Stowaway VII subfamily of MITE transposable elements in the rice genome, cloning the amplification products and applying the cloned inserts to an array as described in Examples above.

First, genomic DNA of four rice cultivars: Azucena, IR64, Millin, Nipponbare (500 ng in total, 125 ng mixed from each cultivar) is digested with MseI restriction enzyme, and MseI adapters (shown below) are ligated to the restriction fragments. Amplification is carried out using the Internal Primer Right and/or Left (below) and MseI adapter Primer 1. After 25 cycles of amplification 1 µl of amplified product is used as a template for another round of amplification using Inverted Repeat Primer and MseI adapter Primer1. Amplification products from this reaction are cloned using a Topo™ cloning kit. The clone inserts are amplified, purified and arrayed on glass slides as in Example 2, resulting in a diversity array comprising 384 clones ready for polymorphism detection. The slides are processed as described in Example 3.

| Primer name | Primer sequence | SEQ ID No |
|---|---|---|
| Internal Stowaway VII Right Primer | 5'-ACCGTGTCGCTGTCCTAAAC-3' | 15 |
| Internal Stowaway VII Left Primer | 5'-ATATTCCCAAGGTTTGACTT-3' | 16 |
| Inverted Repeat Primer | 5'-CTTTACGAGTATGGAGGGAG-3' | 17 |
| MseI adapter Primer 1 | 5'-CTCGTAGACTGCGTACC-3' | 18 |
| MseI adapter Primer 2 | 5'-TACTCAGGACTCAT-3' | 19 |

Diversity panels are generated from each cultivar separately using the method above and are labeled with a fluorescent dye (Cy3 for Azucena and Cy5 for IR64). Labeled panels are hybridized to the diversity arrays and washed. Fluorescent images are captured using GMS 418 Scanner (Affymetrix, CA USA) and analyzed using the methods described above. Based on other experimental data, about 17% of the features are expected to be polymorphic.

Example 13

Analysis of Polymorphisms in Rice using Diversity Panels Generated by Semi-Random Amplification As an alternative, diversity panels can be generated without the need for a restriction digestion and adapter ligation step. This offers the possibility of a complete automation of this invention. In this example, diversity panels are generated by a semi-random, two-step amplification protocol (ST-PCR; Chun et al., *Yeast* 15: 233–40, 1997). ST-PCR requires only genomic DNA and two pairs of amplification primers used in two successive amplification reactions.

Genomic DNA (300 ng total) from two rice cultivars, Azucena and IR64, is used as a template for amplification using two primers: Internal Stowaway VII Right Primer (see table above for sequence) and ST-PCR1d Primer (5'-

GGCCACGCGTCGACTAGTACN$_{10}$TCGAG-3') (SEQ ID No: 20). Amplification is performed using 0.5 unit Red Taq™ polymerase (Sigma) and using a hot start program in which the polymerase is added after the first step of the program. The program uses the following steps: (1) 95° C. for 3 min; 80° C. for 2 min; (2) 94° C. for 30 s; (3) 42° C. for 30 s and −1.0° C. for each subsequent cycle; (4) 72° C. for 3 min; (5) repeat steps 2–4 five times; (6) 94° C. for 30 s; (7) 65° C. for 30 s; (8) 72° C. for 3 min; (9) repeat steps 6–8 for 24 more times; (10) hold at 4° C.

After completion of this first amplification program, the product is diluted 1:4 with water and 1 μl is removed for a second amplification. In the second amplification reaction, Inverted Repeat Primer (see Table above) and ST-PCR2 primer (5'-GGCCACGCGTCGACTAGTAC-3' SEQ ID No: 21) are used in the following program: 35 cycles of 94° C. for 30 sec; 65° C. for 30 s; 72° C. for 3 min; followed by a hold at 4° C. The amplification products are cloned. Diversity Panels are scaled up as described in Example 1 and diversity arrays are prepared as in Example 2.

Diversity panels are generated from each cultivar separately using the method above and are labeled with fluorescent dye (Cy3 for Azucena and Cy5 for IR64). Labeled panels are hybridized to diversity arrays slides and washed. Fluorescent images are captured using GMS 418 Scanner, and images are analyzed using the methods described above. Based on other experimental data, about 17% of the features are expected to be polymorphic.

Example 14
Application of Diversity Array Technology to Determine DNA Methylation Patterns in Rice Analysis of the cytosine methylation status at the CpG dinucleotide and CpXpG trinucleotide within the sequence CCGG in the rice genome is performed using diversity array technology. For the analysis of developmental variation in methylation status among rice tissues, 11 tissues of rice cultivar Millin are collected. These tissues are: (1) 4-week old seedling leaves, (2) 4-week old seedling roots, (3) mature pollen and anther, (4) immature pollen and anther, (5) fertilized ovary and stigma, (6) unfertilized ovary and stigma, (7) mature embryo, (8) immature embryo, (9) immature endosperm, (10) flag leaves and (11) 3-week callus.

Genomic DNA is isolated from these tissues and a mixed sample of DNA is completely digested with MspI or HpaII, both methylation sensitive. Diversity panels from MspI-digested and HpaII-digested DNA are prepared using the methods described in Example 1 (using MspI adapter and MspI primer sequences presented in Table 1). The diversity panels are scaled up as described in Example 1 and diversity arrays are prepared as in Example 2.

Diversity panels from the various tissues are labeled with either Cy3 or Cy5 and hybridized to the diversity array as described in Examples 4 and 5. Differentially methylated regions in DNA between two tissues are identified as array features that have Cy3/Cy5 signal ratio ≧3.0 or ≦0.33. A portion of a diversity array from two such comparisons are presented in FIG. 13 showing clear differences in hybridization signal for a number of array features among the tissues compared Differences in methylation patterns among the tissues analyzed are also identified through comparison of normalized ratios of signal intensity for a specific tissue. The signal is normalized to the signal obtained from hybridization with labeled TOPO vector sequence. Statistical methods described herein are used to identify the features with developmentally regulated pattern of cytosine methylation. A number of tissue specific CpG methylation patterns at CCGG sites are confirmed by Southern analysis in which DNA from the diversity panels are hybridized with labeled insert from a clone identified as differentially methylated in fertilized ovary and stigma. One such example is presented in FIG. 14. The absence of hybridization in lane 5 confirms the low value of hybridization obtained from the normalized data (FIG. 14). In addition, DNA sequences are determined for 20 of the tissue methylation polymorphic fragments. One of the fragments has high sequence identity with the rice chloroplast genome and the rest of the fragments are derived from the nuclear genome.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of genotyping, comprising the steps of:
(a) generating a first diversity panel from nucleic acid molecules of two or more organisms, wherein the first diversity panel comprises a reproducible pattern of nucleic acid molecules;
(b) separating the nucleic acid molecules of the first diversity panel on the basis of sequence or molecular weight;
(c) placing the separated nucleic acid molecules into an addressable array;
(d) generating a second diversity panel from nucleic acid molecules of an organism, wherein the second diversity panel comprises a reproducible pattern of nucleic acid molecules;
(e) hybridizing the second diversity panel to the addressable array; and
(f) detecting hybridization, therefrom determining a pattern of hybridization;
wherein the genotype of the second organism is determined from the hybridization pattern.

2. The method of claim 1, wherein the first diversity panel is generated by amplification.

3. The method of claim 1, wherein the second diversity panel is generated by amplification.

4. The method of claim 1, wherein the first diversity panel is cDNA.

5. The method of claim 1, wherein the second diversity panel further comprises a detectable molecule.

6. The method of claim 1, further comprising generating additional diversity panels, wherein each additional diversity panel is generated from nucleic acid molecules of an organism, wherein each diversity panel comprises a reproducible pattern of nucleic acid molecules.

7. The method of claim 6, wherein the second and additional diversity panels further comprise a detectable molecule, wherein the detectable molecule of each diversity panel can be distinguished from the detectable molecule of the other diversity panels.

8. The method of either one of claims 4 or 6, wherein the detectable molecule is selected from the group consisting of a fluorochrome, a mass spectrometry tag, a chemiluminescent molecule and a radioactive molecule.

9. The method of either one of claims 2 or 3, wherein the amplification is performed using a single primer.

10. The method of either one of claims 2 or 3, wherein the amplification is performed using a primer pair, wherein one of the primers anneals to a sequence that is conserved among a family of insertion elements.

11. The method of claim 1, wherein the first or second or both diversity panels are generated by the steps comprising: digesting the nucleic acids of the organisms with one or more restriction enzymes to generate fragments, ligating adapter sequences to the fragments, and amplifying the ligated fragments using a primer that anneals to the adapter sequence.

12. The method of claim 11, wherein the restriction enzyme is methylation sensitive.

13. The method of claim 1, wherein the first or second or both diversity panels are generated by the steps comprising: digesting the nucleic acids of the organisms with a restriction enzyme to generate fragments, ligating an adapter sequence to the fragments, and amplifying the ligated fragments using a primer pair, wherein one primer anneals to at least part of the adapter sequence and the other primer anneals to a sequence that is conserved among a family of insertion elements.

14. The method of claim 1, wherein the first or second or both diversity panels are generated by digestion of the nucleic acid molecules with one or more restriction enzymes and size selection of the digested nucleic acids.

15. The method of either of claims 2 or 3, wherein the amplification method is amplified fragment-length polymorphism (AFLP) or random-amplified polymorphic DNA (RAPD).

16. The method of claim 1, wherein the nucleic acid of the organisms is genomic DNA, mitochondrial DNA, chloroplast DNA or mRNA.

17. The method of claim 1, wherein the organism of step (d) is the same as one of the organisms of step (a).

18. The method of claim 1, wherein the organisms of step (a) are from the same species.

19. The method of claim 1, wherein the organisms of step (a) are selected from the group consisting of plants, bacteria, viruses, fungi, animals and humans.

20. The method of claim 1, wherein the organisms of step (a) are plants selected from the group consisting of wheat, rice, corn, barley, Arabidopsis, potato, cassava, banana, yam, cowpea, apple, pear, orange, walnut, brazil nut, pecan, lentil, pea and rye.

21. The method of claim 1, wherein the addressable array is on a silicon chip or a glass slide.

22. The method of claim 1, wherein the detecting step detects the presence or absence of hydridization.

* * * * *